(12) United States Patent
Funakoshi et al.

(10) Patent No.: US 9,974,795 B2
(45) Date of Patent: May 22, 2018

(54) ANTICANCER AGENT COMPOSITION

(71) Applicant: CARNA BIOSCIENCES, INC., Hyogo (JP)

(72) Inventors: Yoko Funakoshi, Hyogo (JP); Chika Tanaka, Hyogo (JP); Tokiko Asami, Hyogo (JP); Masaaki Sawa, Hyogo (JP)

(73) Assignee: CARNA BIOSCIENCES, INC., Hyogo (JP)

(*) Notice: Subject to any disclaimer, the term of this patent is extended or adjusted under 35 U.S.C. 154(b) by 0 days. days.

(21) Appl. No.: 15/115,606

(22) PCT Filed: Jan. 26, 2015

(86) PCT No.: PCT/JP2015/051987
§ 371 (c)(1),
(2) Date: Jul. 29, 2016

(87) PCT Pub. No.: WO2015/115355
PCT Pub. Date: Aug. 6, 2015

(65) Prior Publication Data
US 2017/0065609 A1    Mar. 9, 2017

(30) Foreign Application Priority Data
Jan. 31, 2014   (JP) .................. 2014-018075

(51) Int. Cl.
| | | |
|---|---|---|
| A61K 31/553 | (2006.01) | |
| A61K 31/496 | (2006.01) | |
| A61K 31/519 | (2006.01) | |
| A61K 31/5377 | (2006.01) | |
| A61K 31/4725 | (2006.01) | |
| A61K 31/444 | (2006.01) | |
| A61K 31/506 | (2006.01) | |
| A61K 31/395 | (2006.01) | |
| A61K 45/06 | (2006.01) | |
| A61K 31/437 | (2006.01) | |

(52) U.S. Cl.
CPC .......... *A61K 31/553* (2013.01); *A61K 31/395* (2013.01); *A61K 31/437* (2013.01); *A61K 31/444* (2013.01); *A61K 31/4725* (2013.01); *A61K 31/496* (2013.01); *A61K 31/506* (2013.01); *A61K 31/519* (2013.01); *A61K 31/5377* (2013.01); *A61K 45/06* (2013.01)

(58) Field of Classification Search
CPC .. A61K 31/553; A61K 31/496; A61K 31/519; A61K 31/5377; A61K 31/4725; A61K 31/444; A61K 31/506; A61K 31/395
USPC .......................................... 546/113; 514/211
See application file for complete search history.

(56) References Cited

U.S. PATENT DOCUMENTS

| | | |
|---|---|---|
| 6,335,342 B1 | 1/2002 | Longo et al. |
| 8,742,113 B2 | 6/2014 | Irie et al. |
| 2003/0158215 A1 | 8/2003 | Tang et al. |
| 2006/0122232 A1 | 6/2006 | Chou et al. |
| 2007/0112020 A1 | 5/2007 | Vanotti et al. |
| 2009/0253679 A1 | 10/2009 | Leroy et al. |
| 2009/0298820 A1 | 12/2009 | Tsou et al. |
| 2014/0018533 A1 | 1/2014 | Irie et al. |

FOREIGN PATENT DOCUMENTS

| | | |
|---|---|---|
| FR | 2907120 A1 | 4/2008 |
| JP | 2002-531500 A | 9/2002 |
| JP | 2002-531503 A | 9/2002 |
| JP | 2006-504632 A | 2/2006 |
| JP | 2008-516903 | 5/2008 |
| JP | 2009-515849 | 4/2009 |
| JP | 2009-531373 A | 9/2009 |
| JP | 2010-505922 | 2/2010 |
| JP | 5659356 B2 | 12/2014 |
| WO | WO 2001/098299 A1 | 12/2001 |
| WO | WO-2004/007504 A1 | 1/2004 |

(Continued)

OTHER PUBLICATIONS

PCT International Search Report & Written Opinion, International Application No. PCT/JP2015/051987, dated Mar. 17, 2015, 18 Pages.
Aarts, M., et al., "Forced Mitotic Entry of S-Phase Cells as a Therapeutic Strategy Induced by Inhibition of WEE1," Cancer Discovery, 2012, pp. 524-539, vol. 2, No. 6.
Barker, C.R., et al., "Inhibition of Hsp90 acts synergistically with topoisomerase II poisons to increase the apoptotic killing of cells due to an increase in topoisomerase II mediated DNA damage," Nucleic Acids Research, 2006, pp. 1148-1157, vol. 34, No. 4.
Bonte, D., et al., "Cdc7-Dbf4 Kinase Overexpression in Multiple Cancers and Tumor Cell Lines Is Correlated with p53 Inactivation," Neoplasia, 2008, pp. 920-931, vol. 10, No. 9.
De Witt Hamer, P.C., et al., "WEE1 Kinase Targeting Combined with DNA-Damaging Cancer Therapy Catalyzes Mitotic Catastrophe," Clinical Cancer Research, 2011, pp. 4200-4207, vol. 17, No. 13.

(Continued)

*Primary Examiner* — Kahsay Habte
(74) *Attorney, Agent, or Firm* — Wenderoth, Lind & Ponack, L.L.P.

(57) ABSTRACT

Provided is a pharmaceutical composition comprising a Cdc7 inhibitor and an M phase promoter. In particular, the Cdc7 inhibitor contained in the pharmaceutical composition is a furanone derivative represented by formula (I), or a pharmaceutically acceptable salt thereof. (In the formula, A is —COOR1 or a hydrogen atom; R1 is a hydrogen atom, an optionally substituted hydrocarbon group, or an optionally substituted heterocycle; R2 and R3 are the same or different and are each a hydrogen atom, an optionally substituted hydrocarbon group, an optionally substituted phenyl group, an optionally substituted heterocycle, an optionally substituted heterocyclic condensed ring, or an optionally substituted amino group. Alternatively, R2 and R3 may, together with the nitrogen atoms bonding the same, form an optionally substituted heterocycle or optionally substituted heterocyclic condensed ring. R4 is a hydrogen atom or halogen atom. However, if A is —COOR1, R2 and R3 are not both simultaneously optionally substituted amino groups. When A is a hydrogen atom, R3 is a hydrogen atom.)

16 Claims, 15 Drawing Sheets

(56) References Cited

FOREIGN PATENT DOCUMENTS

| WO | WO 2005/009370 A2 | 2/2005 |
|---|---|---|
| WO | WO 2005/013986 A1 | 2/2005 |
| WO | WO 2005/014572 A1 | 2/2005 |
| WO | WO 2006/037875 A1 | 4/2006 |
| WO | WO 2007/054508 A1 | 5/2007 |
| WO | WO 2008/046982 A3 | 4/2008 |
| WO | WO 2008/109443 A2 | 9/2008 |
| WO | WO 2009/155052 A1 | 12/2009 |
| WO | WO 2010/030727 A1 | 3/2010 |
| WO | WO 2011/008915 A1 | 1/2011 |
| WO | WO 2012/002568 A1 | 1/2012 |
| WO | WO 2012/133802 A1 | 10/2012 |
| WO | WO-2015/115355 A1 | 8/2015 |

OTHER PUBLICATIONS

Do, K., et al., "Wee1 kinase as a target for cancer therapy," Cell Cycle, 2013, pp. 3159-3164, vol. 12, No. 19.
Guertin, A.D., et al., "Preclinical Evaluation of the WEE1 Inhibitor MK-1775 as Single-Agent Anticancer Therapy," Molecular Cancer Therapeutics, 2013, pp. 1442-1452, vol. 12, No. 8.
Ito, S., et al., "Cellular dynamics and functions of human Cdc7 kinase," Journal of Japanese Biochemical Society, 2007, pp. 1P-0696, abstract CD.
Ito, S., et al., "Mechanism of cancer cell death induced by depletion of an essential replication regulator," PLoS One, 2012, pp. 1-14, e36372, vol. 7, No. 5.
Kreahling, J.M., et al., "Wee1 Inhibition by MK-1775 Leads to Tumor Inhibition and Enhances Efficacy of Gemcitabine in Human Sarcomas," PLoS One, 2013, vol. 8, No. 3, e57523.
Kulkarni, A.A., et al., "Cdc7 Kinase is a Predictor of Survival and a Novel Therapeutic Target in Epithelial Ovarian Carcinoma," Clinical Cancer Research, 2009, pp. 2417-2425, vol. 15, No. 7.
Masai, H., et al., "Cdc7 Kinase Complex: A Key Regulator in the Initiation of DNA Replication," Journal of Cellular Physiology, 2002, pp. 287-296, vol. 190.
Masai, H., "Control of initiation/progression of the S-phase and diseases," Inflammation & Immunology, 2009, pp. 165-172, vol. 17, No. 2.
Montagnoli, A., et al., "Cdc7 Inhibition Reveals a p53-Dependent Replication Checkpoint That is Defective in Cancer Cells," Cancer Research, 2004, pp. 7110-7116, vol. 64.
Montano, R., et al., "Preclinical Development of the Novel Chk1 Inhibitor SCH900776 in Combination with DNA-Damaging Agents and Antimetabolites," Molecular Cancer Therapeutics, 2012, pp. 427-438, vol. 11, No. 2.
Rodriguez-Acebes, S., et al., "Targeting DNA Replication before it Starts, Cdc7 as a Therapeutic Target in p53-Mutant Breast Cancers," The American Journal of Pathology, 2010, pp. 2034-2045, vol. 177, No. 4.
Sawa, M., et al., "Drug design with Cdc7 kinase: a potential novel cancer therapy target," Drug Design, Development and Therapy, 2008, pp. 255-264, vol. 2.
Skoura, E., et al., "Preclinical Research in Treatment of Pancreatic Cancer," Journal of the Pancreas, 2013, pp. 384-387, vol. 14, No. 4.
PCT International Search Report & Written Opinion, International Application No. PCT/JP2012/058636, dated Apr. 24, 2012, 15 Pages.
European Patent Office, Supplementary European Search Report, European Patent Application No. 12763979.7, dated Jul. 17, 2014, 5 Pages.
European Patent Office, First Office Action, European Patent Application No. 12763979.7, dated Jul. 1, 2016, 4 Pages.
European Patent Office, Second Office Action, European Patent Application No. 12763979.7, dated Apr. 5, 2017, 5 Pages.
Intellectual Property Australia, Examination Report, Australian Patent Application No. 2012233246, dated Apr. 4, 2016, 3 Pages.
Japanese Patent Office, Office Action, Japanese Patent Application No. 2016-020407, dated Jan. 10, 2017, 4 Pages.
Greene, T.W., et al., "Cleavage of Esters," Protective Groups in Organic Synthesis, 3rd Edition, 1999, pp. 377-380.
Iwasaki, T., et al., "Transesterification of Various Methyl Esters Under Mild Conditions Catalyzed by Tetranuclear Zinc Cluster," J. Org. Chem., 2008, pp. 5147-5150, vol. 73, No. 13.
Kim, J.M., et al., "Cdc7 kinase mediates Claspin phosphorylation in DNA replication checkpoint," Oncogene, 2008, pp. 3475-3482, vol. 27, No. 24.
Kuo, S., et al., "Studies on Heterocyclic Compounds. IX. Synthesis and Antiallergic Activity of Furo[2,3-b] [1,8]naphthyridine-3,4(2H,9H)-diones and 4H-Furo[2,3-d]pyrido[1,2-a]-pyrimidine-3,4(2H)-diones," Chem. Pharm. Bull., 1988, pp. 4403-4407, vol. 36, No. 11.
Kuo, S., et al., "Studies on Heterocyclic Compounds. X. Dealkoxycarbonylation of Ethyl 2-Arylamino-4-oxo-4,5-dihydrofuran-3-carboxylates," Chem. Pharm. Bull, 1990, pp. 340-341, vol. 38, No. 2.
Mack, R. A., et al., "Drug-Induced Modifications of the Immune Response. 12. 4,5-Dihydro-4-oxo-2-(substituted amino)-3-furancarboxylic Acids and Derivatives as Novel Antiallergic Agents," J. Med. Chem., 1988, pp. 1910-1918, vol. 31, No. 10.
Patani, G. A., et al., "Bioisosterism: A Rational Approach in Drug Design," Chem. Rev., 1996, pp. 3147-3176, vol. 96.
Extended European Search Report for European Patent Application No. EP 15743649.4, dated Sep. 1, 2017, 9 Pages.
Irie, T., "Discovery of novel furanone derivatives as potent Cdc7 kinase inhibitors," European Journal of Medicinal Chemistry, Feb. 2017, pp. 406-418, vol. 130.

[Fig. 1]
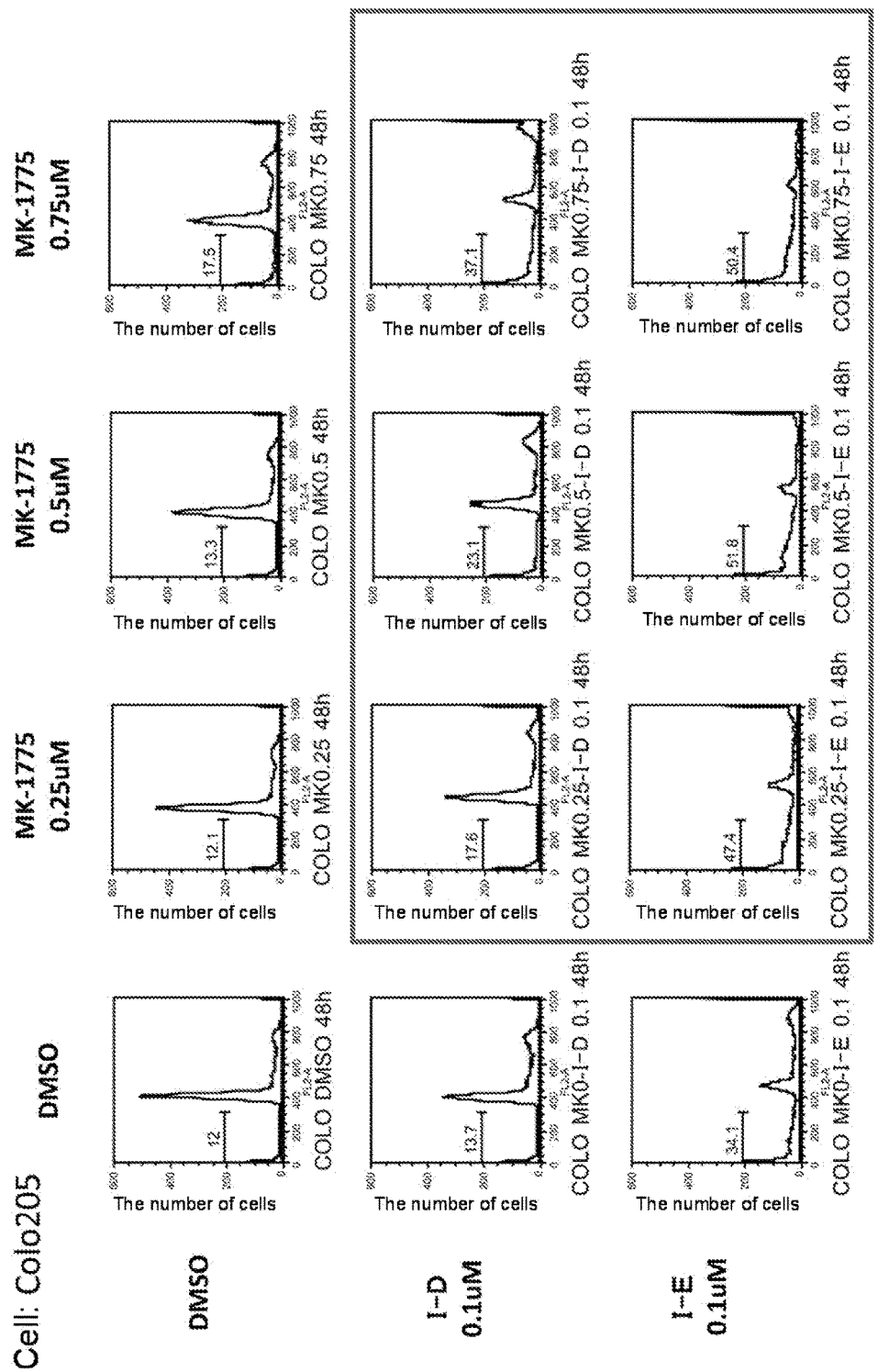

[Fig. 2]
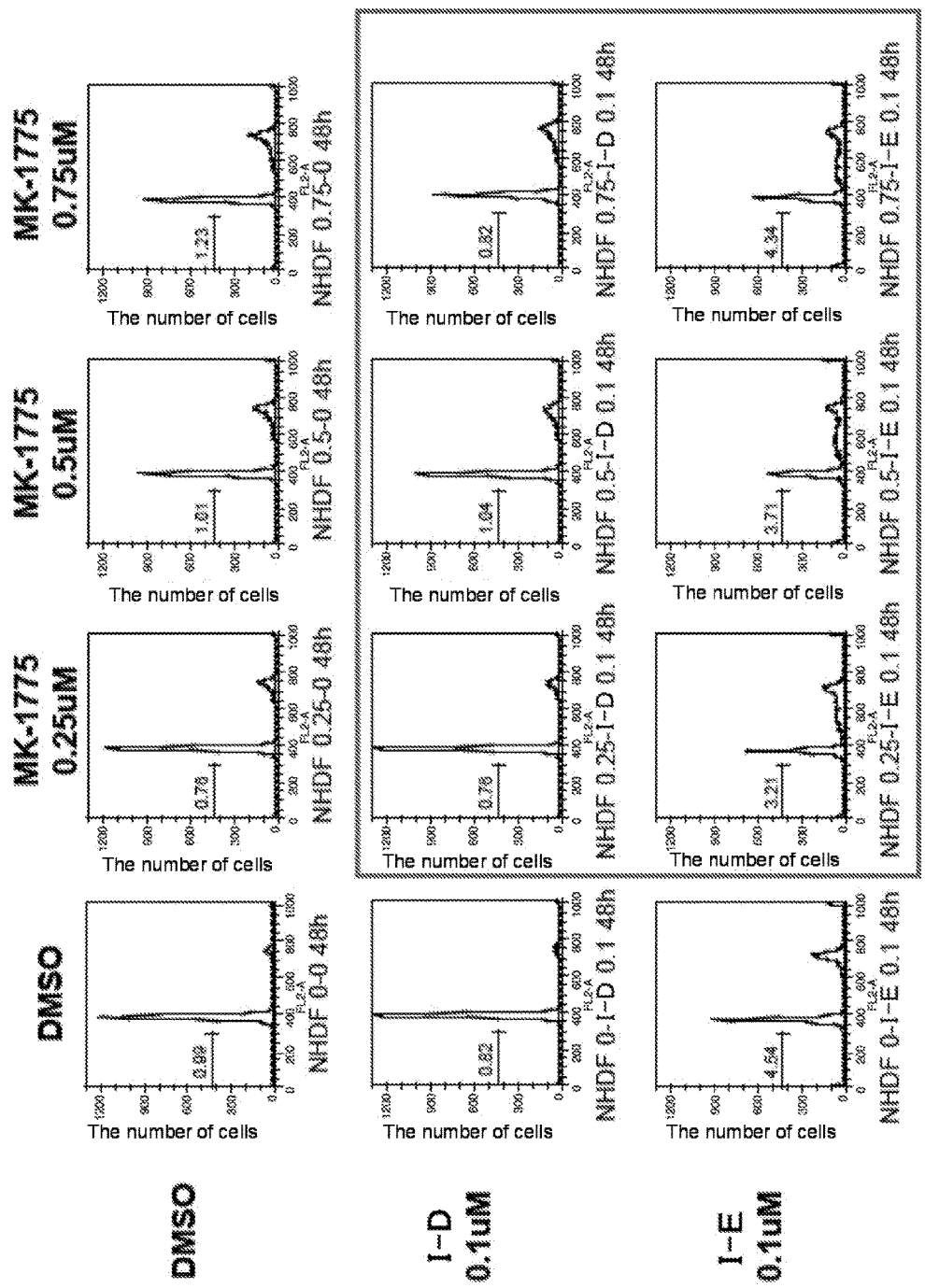

[Fig. 3]
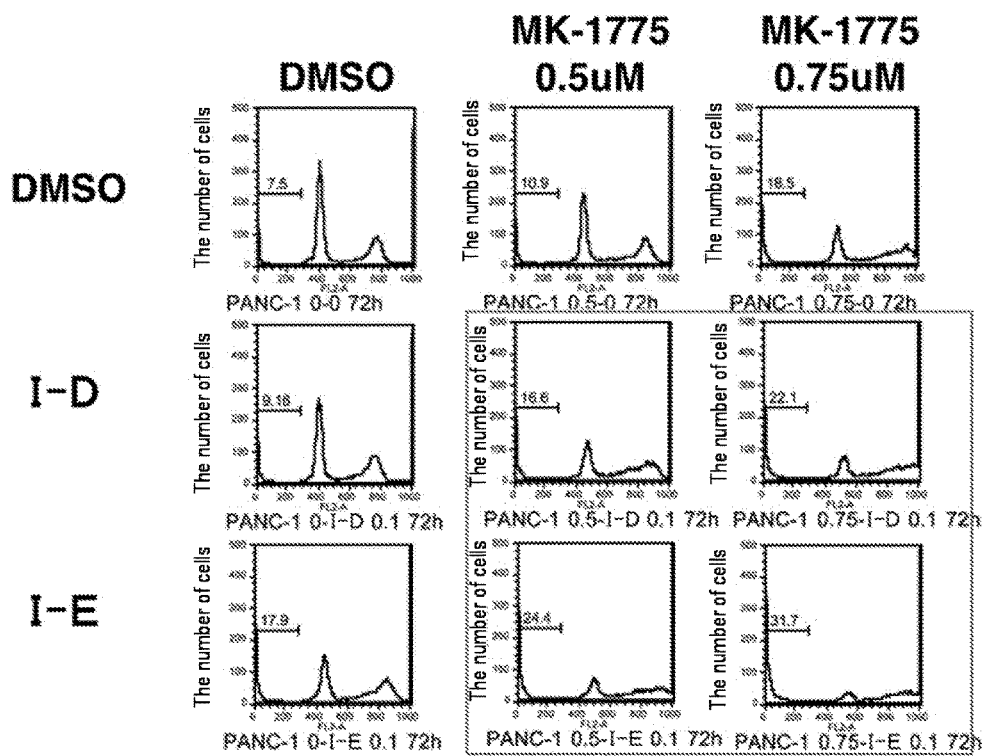

[Fig. 4]
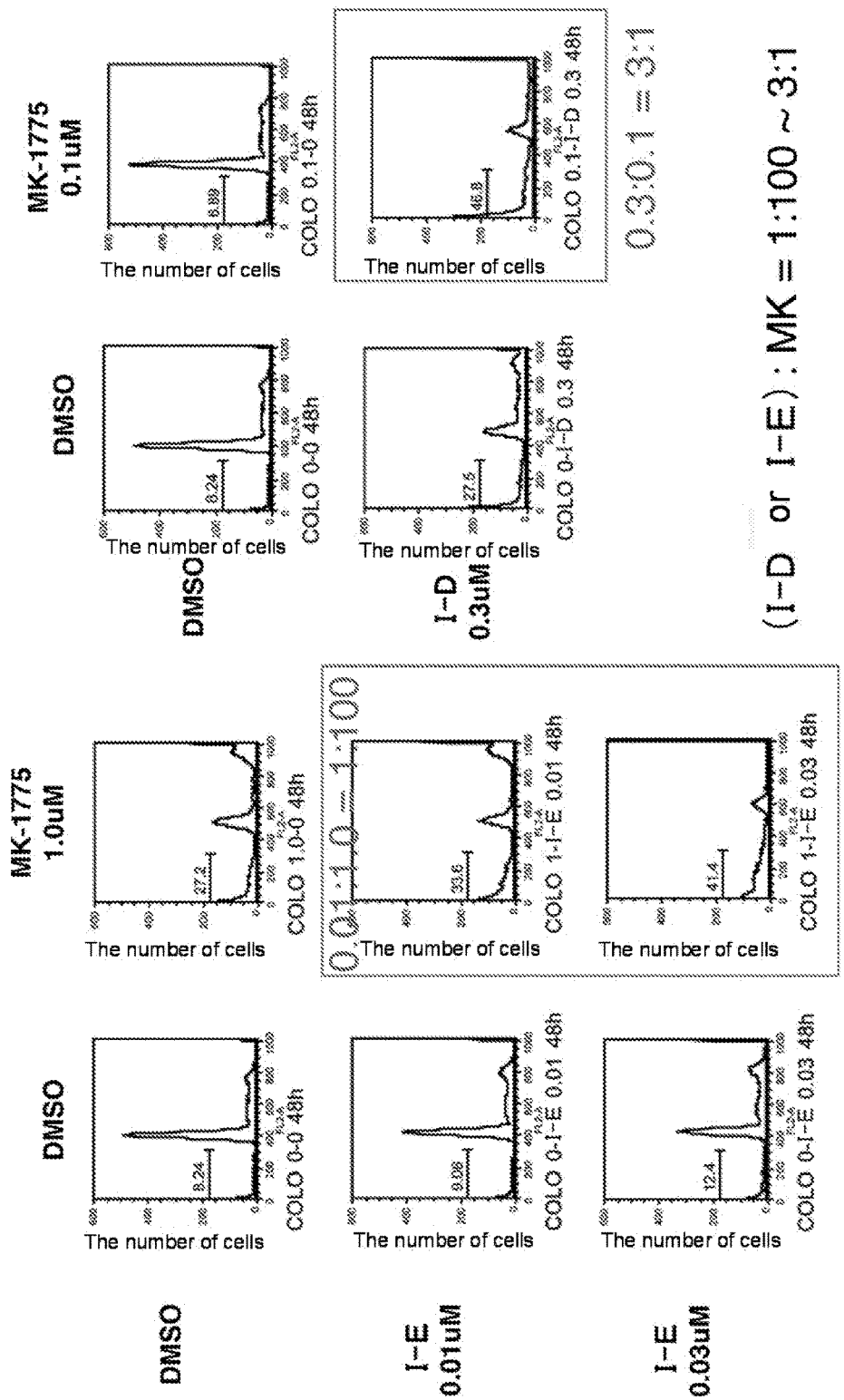

[Fig. 5]
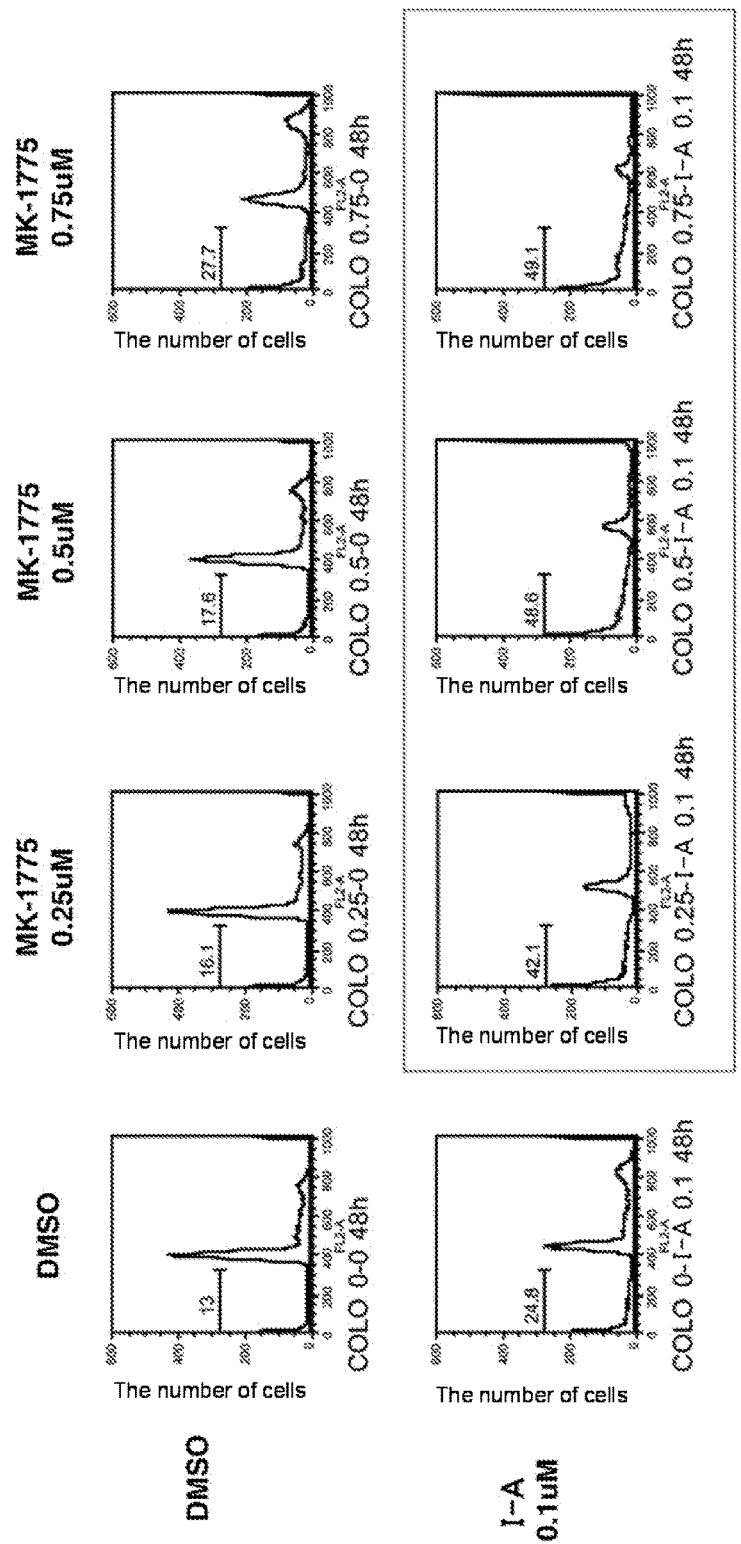

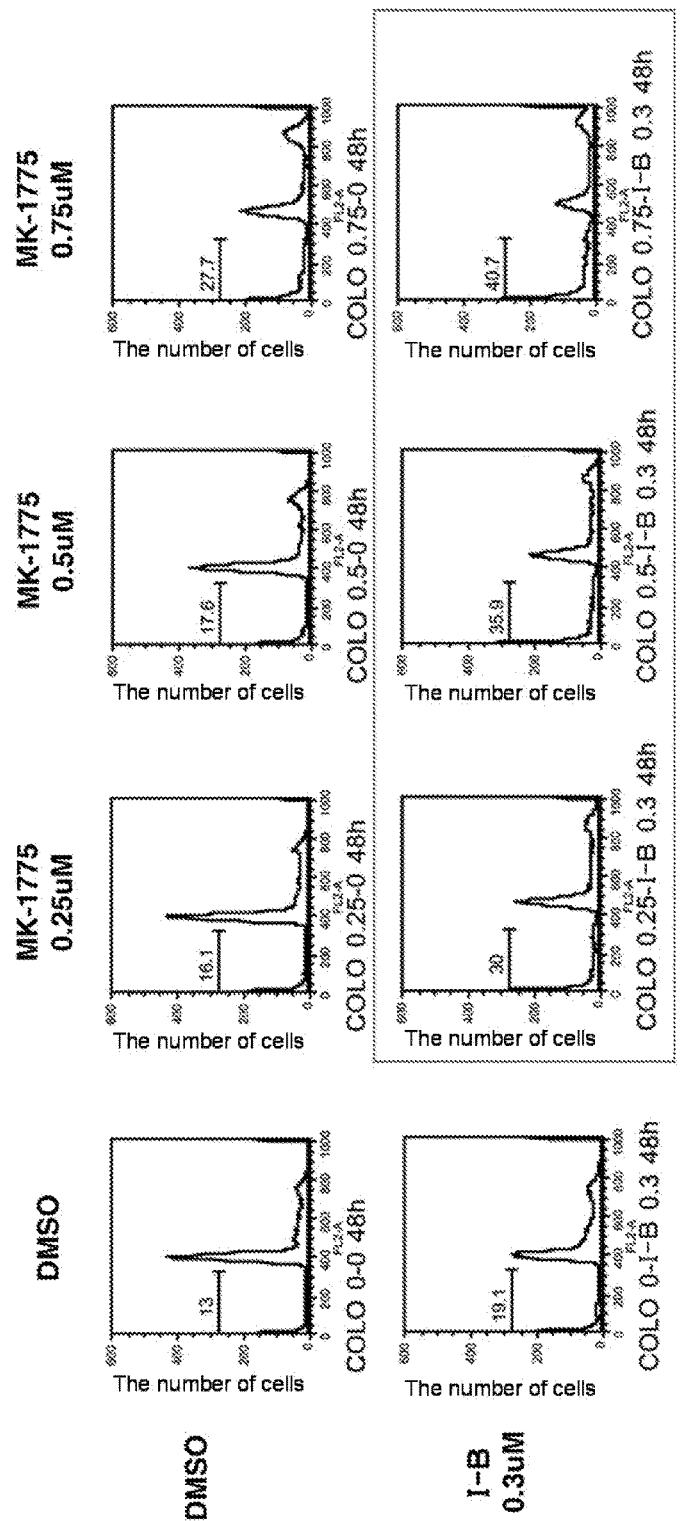
[Fig. 6]

[Fig. 7]
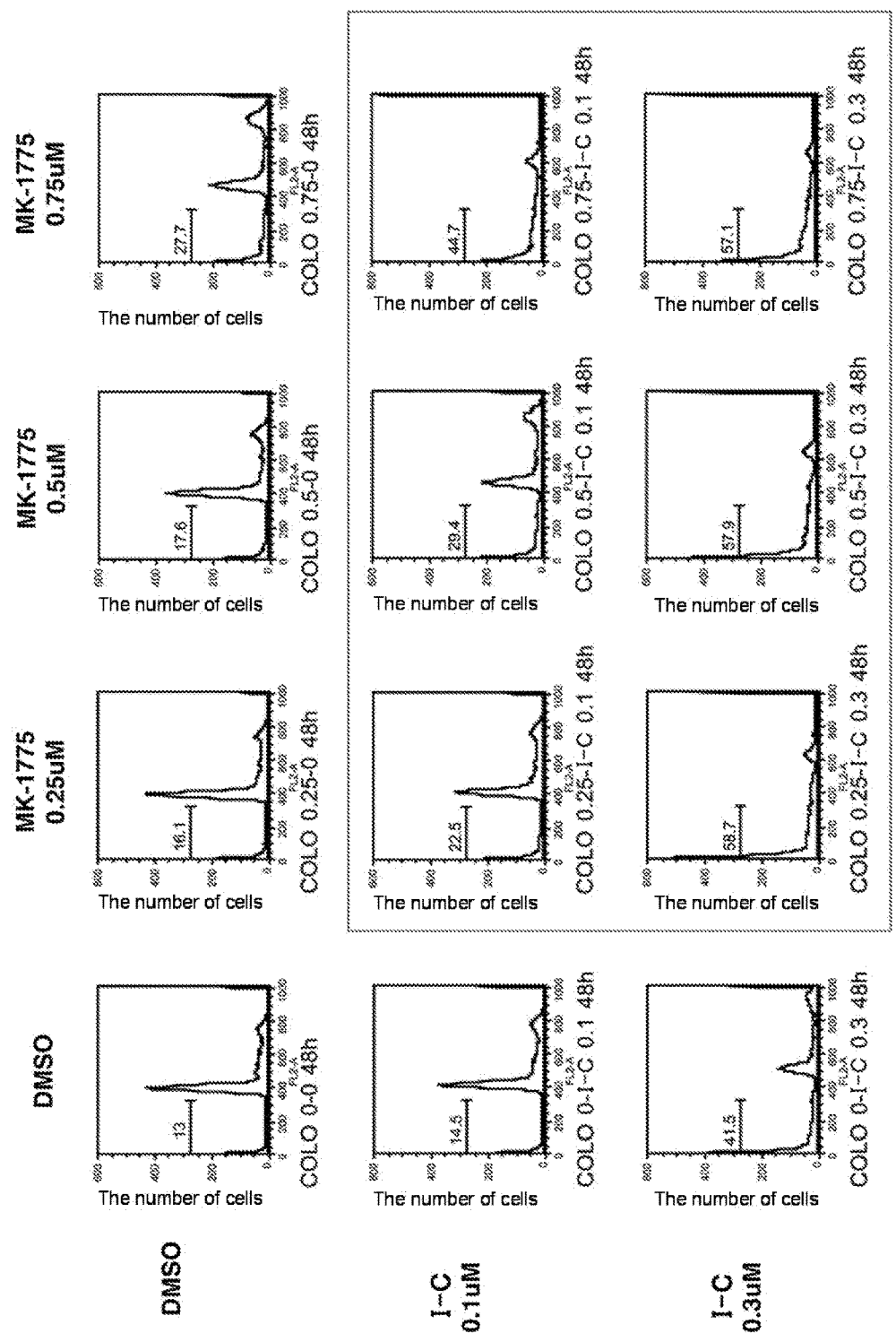

[Fig. 8]
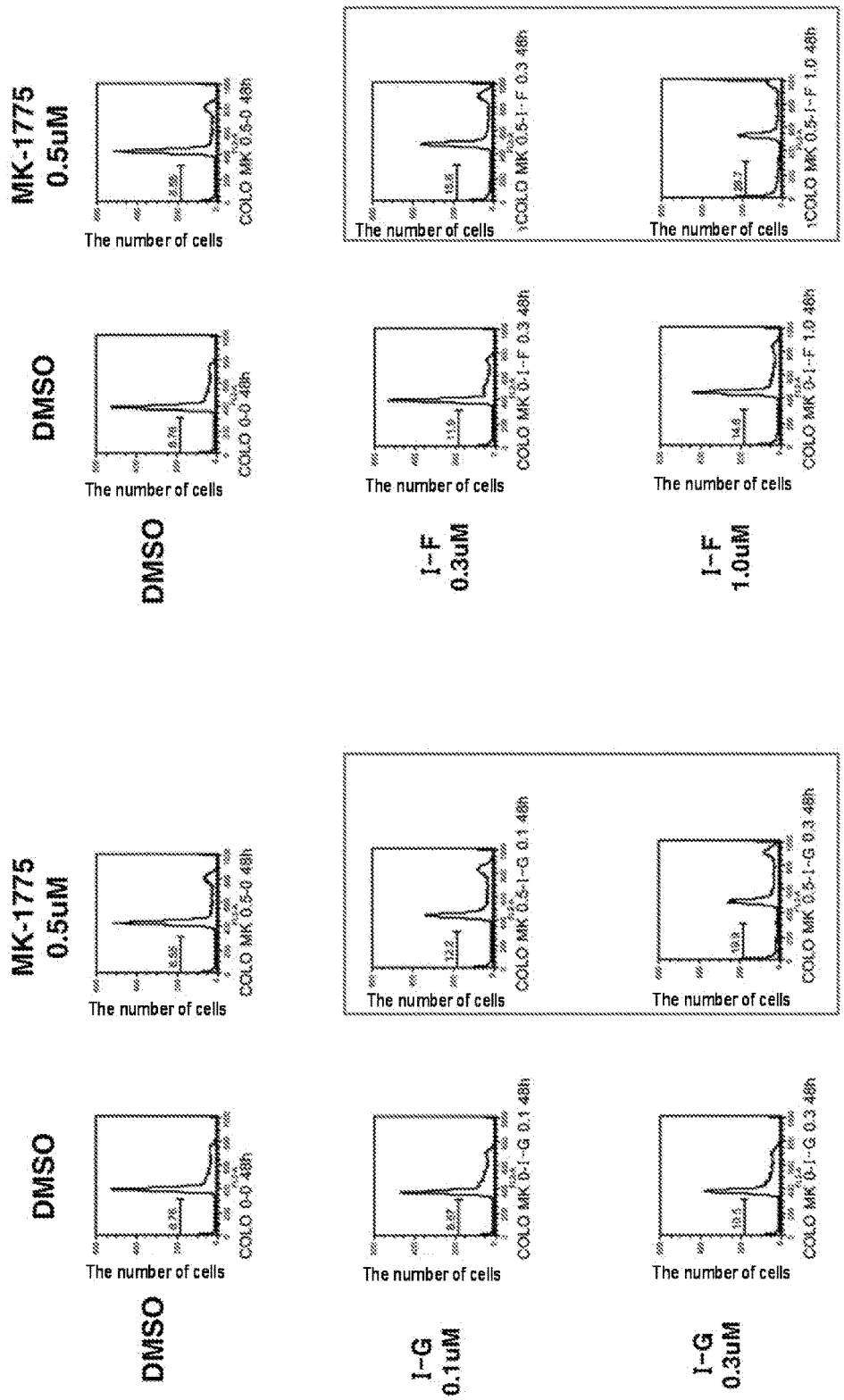

[Fig. 9]
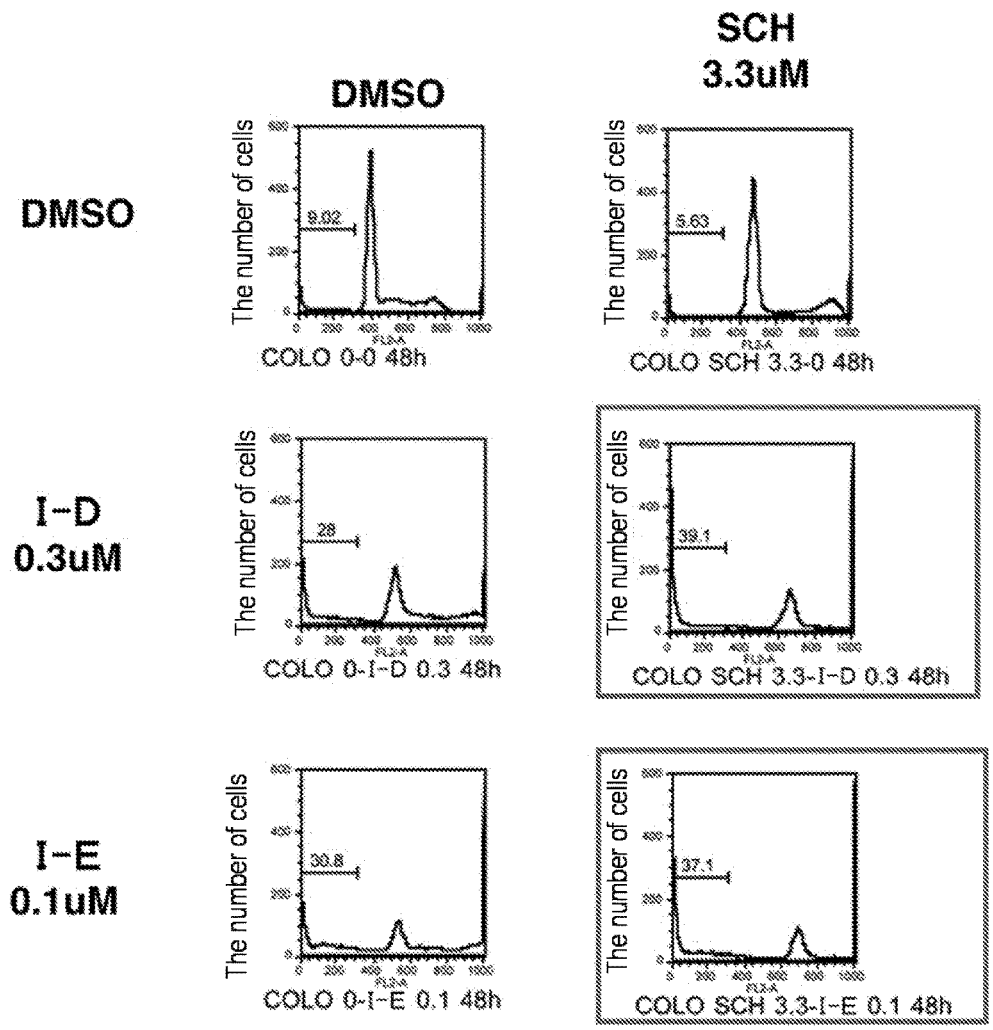

[Fig. 10]
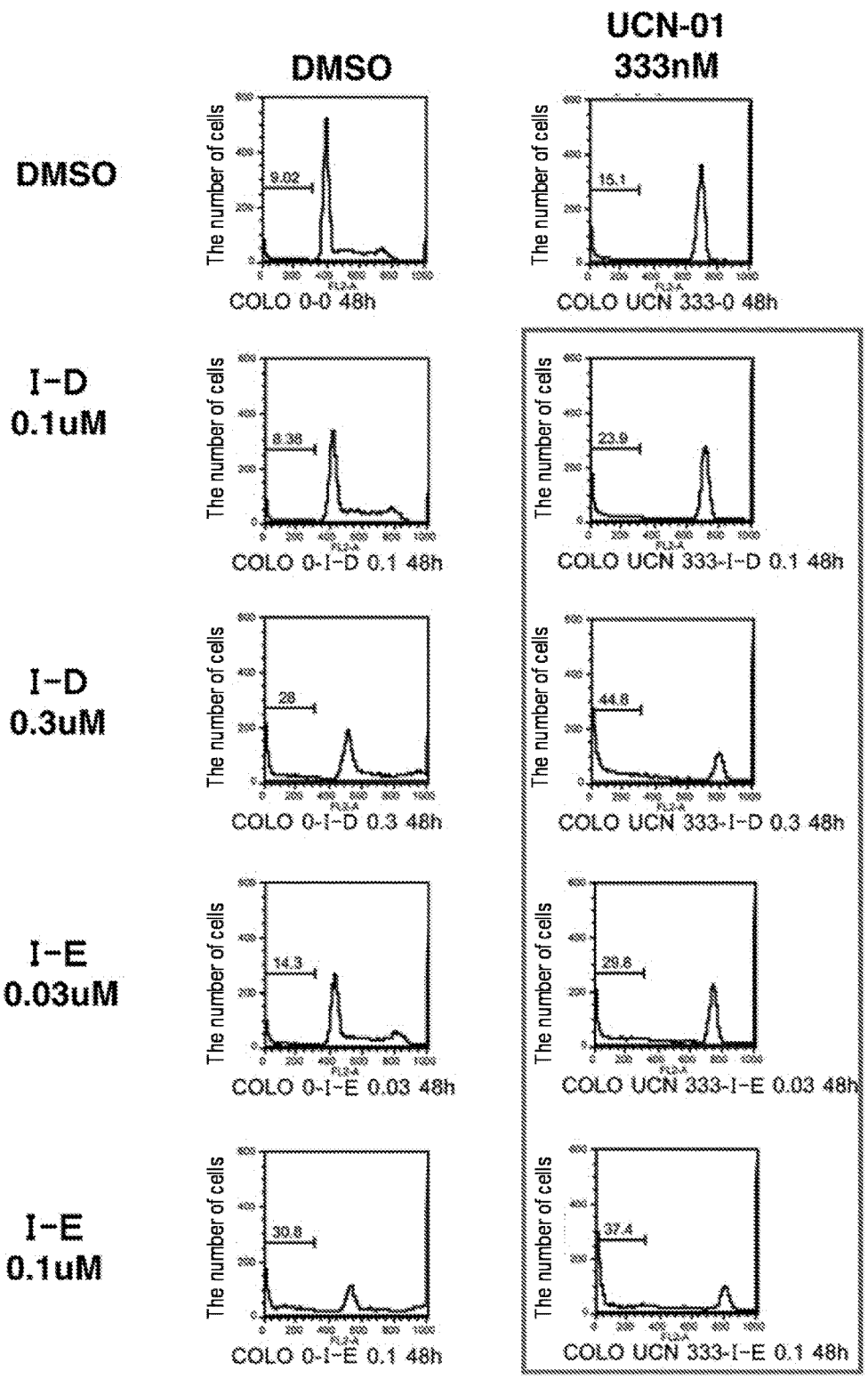

[Fig. 11]
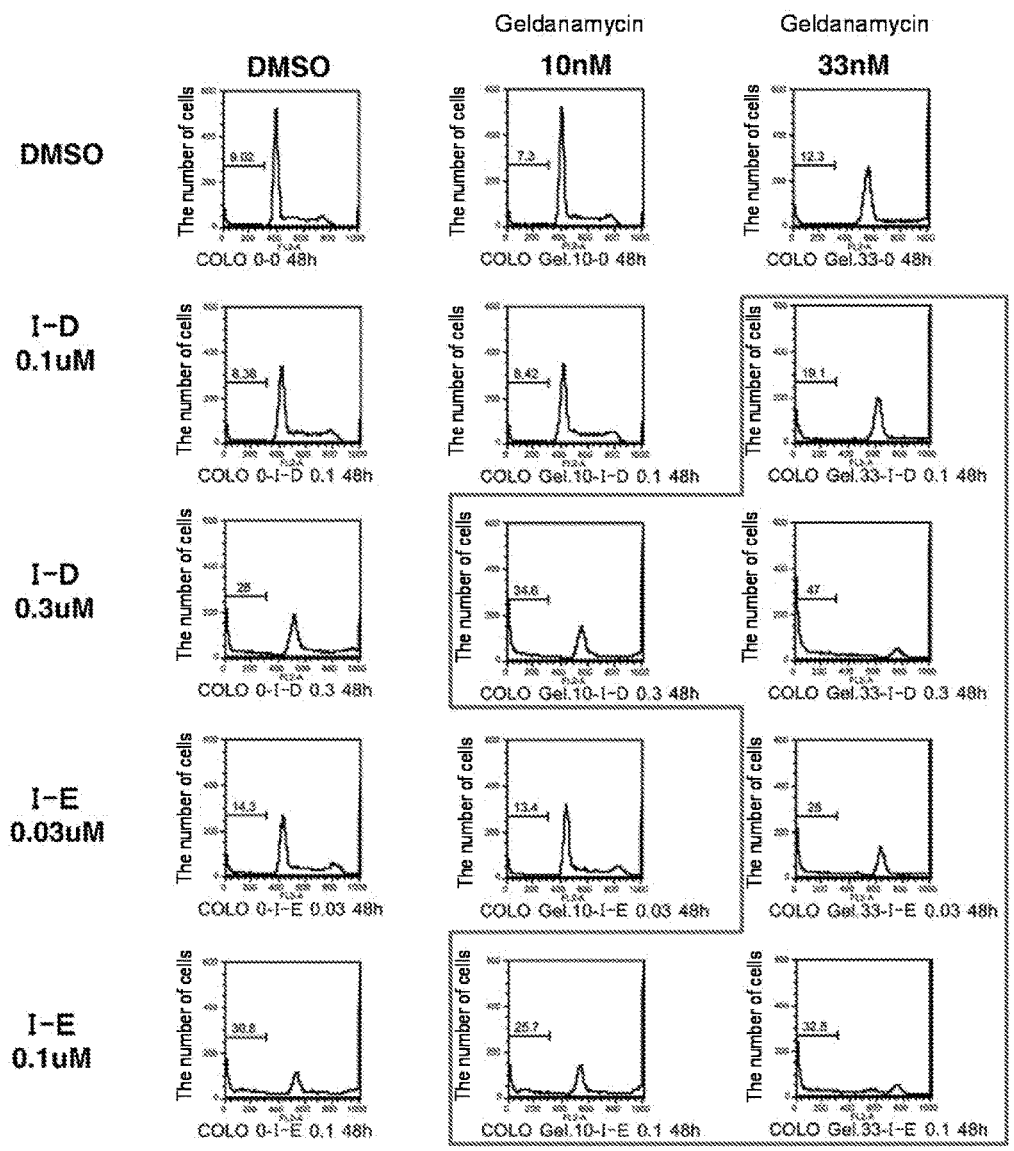

[Fig. 12]

| MK-1775 (nM) | I–D (nM) | | | | | | | | | | |
|---|---|---|---|---|---|---|---|---|---|---|---|
| | 0 | 19.5 | 39.1 | 78.1 | 156 | 313 | 625 | 1250 | 2500 | 5000 | 10000 |
| 1000 | 111 | 112 | 111 | 112 | 112 | 112 | 112 | 112 | 112 | 113 | 114 |
| 500 | 108 | 108 | 107 | 108 | 107 | 108 | 109 | 108 | 109 | 111 | 114 |
| 250 | 104 | 103 | 103 | 102 | 101 | 103 | 102 | 103 | 106 | 112 | 114 |
| 125 | 99 | 98 | 97 | 97 | 97 | 97 | 97 | 99 | 104 | 112 | 115 |
| 62.5 | 75 | 77 | 80 | 82 | 83 | 86 | 90 | 93 | 102 | 113 | 115 |
| 31.3 | 17 | 18 | 22 | 36 | 47 | 62 | 73 | 86 | 99 | 112 | 115 |
| 15.6 | -3 | -1 | -1 | 21 | 38 | 49 | 60 | 81 | 98 | 112 | 115 |
| 7.81 | -3 | -1 | -1 | 5 | 14 | 28 | 52 | 77 | 96 | 111 | 114 |
| 0 | 0 | -1 | 2 | 4 | 10 | 25 | 48 | 77 | 99 | 112 | 115 |

[Fig. 13]

| | | 0 | 19.5 | 39.1 | 78.1 | 156 | 313 | 625 | 1250 | 2500 | 5000 | 10000 |
|---|---|---|---|---|---|---|---|---|---|---|---|---|
| MK-1775 (nM) | 1000 | 112 | 113 | 113 | 113 | 114 | 114 | 115 | 115 | 115 | 115 | 113 |
| | 500 | 109 | 109 | 108 | 110 | 111 | 113 | 114 | 115 | 115 | 115 | 112 |
| | 250 | 105 | 104 | 104 | 106 | 107 | 110 | 112 | 114 | 115 | 115 | 113 |
| | 125 | 100 | 99 | 101 | 102 | 103 | 107 | 109 | 112 | 115 | 115 | 113 |
| | 62.5 | 80 | 92 | 93 | 99 | 101 | 103 | 105 | 109 | 115 | 116 | 114 |
| | 31.3 | 21 | 59 | 73 | 89 | 95 | 96 | 99 | 103 | 114 | 115 | 113 |
| | 15.6 | -1 | 25 | 48 | 74 | 87 | 93 | 96 | 98 | 112 | 115 | 113 |
| | 7.81 | -2 | 12 | 33 | 63 | 85 | 92 | 94 | 98 | 111 | 115 | 112 |
| | 0 | 0 | -1 | 2 | 4 | 10 | 25 | 48 | 77 | 99 | 112 | 115 |

| MK-1775 (nM) \ I-D (nM) | 0 | 19.5 | 39.1 | 78.1 | 156 | 313 | 625 | 1250 | 2500 | 5000 | 10000 |
|---|---|---|---|---|---|---|---|---|---|---|---|
| 1000 | 0 | 0 | 0 | 0 | 1 | 3 | 6 | 10 | 12 | 14 | 16 |
| 500 | 0 | 0 | -1 | 0 | 0 | 2 | 4 | 6 | 9 | 12 | 15 |
| 250 | 0 | -2 | -1 | -2 | -3 | -1 | 0 | 2 | 5 | 12 | 15 |
| 125 | 0 | -1 | -2 | -1 | -2 | -2 | -2 | -1 | 4 | 12 | 14 |
| 62.5 | 0 | 3 | 4 | 6 | 6 | 5 | 3 | 6 | 2 | 10 | 11 |
| 31.3 | 0 | 2 | 3 | 15 | 21 | 25 | 16 | 5 | 0 | 2 | 3 |
| 15.6 | 0 | 4 | 0 | 20 | 31 | 27 | 14 | 1 | -1 | 0 | -1 |
| 7.81 | 0 | 3 | 0 | 4 | 6 | 5 | 6 | 0 | -3 | -1 | -2 |
| 0 | 0 | 0 | 0 | 0 | 0 | 0 | 0 | 0 | 0 | 0 | 0 |

[Fig. 15]

| MK-1775 (nM) \ I–E (nM) | 0 | 19.5 | 39.1 | 78.1 | 156 | 313 | 625 | 1250 | 2500 | 5000 | 10000 |
|---|---|---|---|---|---|---|---|---|---|---|---|
| 1000 | 0 | 1 | 1 | 2 | 3 | 6 | 9 | 13 | 15 | 17 | 15 |
| 500 | 0 | 0 | 0 | 1 | 3 | 6 | 9 | 12 | 15 | 16 | 14 |
| 250 | 0 | -1 | -1 | 1 | 2 | 6 | 9 | 12 | 15 | 16 | 14 |
| 125 | 0 | -1 | 1 | 2 | 3 | 7 | 9 | 12 | 15 | 15 | 13 |
| 62.5 | 0 | 11 | 13 | 17 | 19 | 17 | 16 | 14 | 15 | 14 | 11 |
| 31.3 | 0 | 39 | 50 | 65 | 66 | 55 | 41 | 21 | 15 | 6 | 1 |
| 15.6 | 0 | 27 | 47 | 71 | 78 | 69 | 49 | 22 | 13 | 3 | -2 |
| 7.81 | 0 | 15 | 32 | 61 | 76 | 69 | 48 | 22 | 12 | 2 | -3 |
| 0 | 0 | 0 | 0 | 0 | 0 | 0 | 0 | 0 | 0 | 0 | 0 |

ANTICANCER AGENT COMPOSITION

CROSS-REFERENCE TO RELATED APPLICATIONS

This application is the National Stage of International Application No. PCT/JP2015/051987, filed Jan. 26, 2015, and claims priority to Japanese patent application no. 2014-01807, filed Jan. 31, 2014, which is herein incorporated in its entirety by reference.

TECHNICAL FIELD

The present invention relates to an anticancer composition. More specifically, the present invention relates to an anticancer composition comprising a Cdc7 inhibitor and an M-phase promoter in combination.

BACKGROUND ART

Cancer is a disease that is caused by the non-limiting growth of cells which have lost the control of the cell cycle. Since cancer cells generally grow faster than normal cells, it is considered that cancer can be treated by the control of cell division and DNA replication. In fact, gemcitabine having a DNA replication inhibitory effect is widely used in the treatment of non-small cell lung cancer, pancreatic cancer, bile duct cancer, urinary bladder cancer, breast cancer, or ovary cancer, etc.

Various proteins are involved in the process of the cell cycle. In general, the biological functions of proteins are regulated by various mechanisms of post-translational modifications. Specifically, methylation, acetylation, glycosylation, phosphorylation, and the like are involved in the functional or structural modifications of proteins. Among these post-translational modifications, the phosphorylation is an important mechanism related to the regulation of many functions such as intracellular signal transduction, cell cycle, and cell death. For example, ⅓ or more of the intracellular proteins of mammalian cells are deemed to be phosphorylated.

Protein kinases are enzymes that catalyze the reaction of bonding a phosphoric acid group to a particular amino acid residue in their substrate proteins. This action of the protein kinases phosphorylates a protein at a particular phosphorylation site. The protein kinases are classified as follows on the basis of the types of amino acids at sites to be phosphorylated:

serine-threonine kinase (which phosphorylates a Ser/S or Thr/T residue) and tyrosine kinase (which phosphorylates Tyr/Y)

Cdc7, a serine-threonine kinase, is an essential protein kinase that participates in the initiation of DNA replication in the cell cycle. Cdc7 forms a complex with a cofactor, such as Dbf4 (ASK), which activates its phosphorylating effect, and phosphorylates a substrate MCM (minichromosome maintenance) protein. This phosphorylation appears to allow Cdc45 and DNA polymerase to assemble on DNA so that an MCM complex is formed to start DNA replication (see Non-Patent Document 1).

In recent years, Cdc7 has received attention as a target of anticancer agents and has been actively studied. For example, Cdc7 has been found to be overexpressed not only in general human tumor-derived cell lines but in cancer cells, such as breast cancer, colon cancer, and lung cancer cells, collected from organisms (see Non-Patent Document 2). Particularly, it has recently been shown that Cdc7 is overexpressed in triple negative (ER-/PR-/Her2-) breast cancer cells having p53 mutation (see Non-Patent Document 3). Cdc7 is thus expected to serve as a promising target for triple negative-type breast cancer, which has been regarded as being difficult to treat. In fact, a Cdc7 expression suppression experiment using an RNA interference technique has demonstrated that the inhibition of Cdc7 expression induces the arrest of the cell cycle of normal cells. More importantly, the inhibition of Cdc7 based on the RNA interference technique inhibited the growth of human tumor cells such as HeLa and HCT116, but was less effective for inhibiting normal cells (normal human skin fibroblasts) (see Non-Patent Document 4).

The deletion of DNA replication factors often brings about cell death to cancer cells. Since Cdc7 is also an essential protein kinase involved in the initiation of DNA replication in the cell cycle, its deletion induces the death of cancer cells, regardless of the status of the p53 gene that controls the suppression of the cell growth cycle involving intracellular DNA repair, cell growth arrest, apoptosis, etc. Masai et al. have utilized a fluorescent probe of recently developed Fucci (fluorescent ubiquitination-based cell cycle indicator) to study cell death induced by the deletion of Cdc7 while observing the progression of the cell cycle at real time (see Non-Patent Document 5). They have showed that the inhibition of Cdc7 induces clear cell cycle response in both of p53-positive and p53-negative cells. Particularly, in the p53-negative cells, the progression of the cell cycle is temporarily arrested in the G2-phase prior to the M-phase so that cyclin B1 and other mitotic control gene products accumulate. Subsequently, the G2-phase proceeds to the abnormal M-phase, and cell death occurs after the mitosis. On the other hand, in the p53-positive cancer cells, cyclin B1 does not accumulate, whereas most of the cancer cells are reportedly killed by transition to the abnormal S-phase after the deletion of Cdc7 (see Non-Patent Document 5).

Thus, inhibitors that selectively inhibit Cdc7 are expected to exhibit an effective therapeutic effect on various cancers. Various compounds having a Cdc7 inhibitory effect have been reported so far (see Patent Document 1). Particularly, furanone derivatives having a Cdc7 inhibitory effect have been reported (see Patent Document 2).

Wee1 is a nuclear protein kinase that belongs to protein kinases of the serine-threonine family and plays a role as a regulator important for the progression of the cell cycle together with a dephosphorylating enzyme Cdc25.

The Wee1 kinase suppresses the activity of Cdk1 kinase through the phosphorylation of its Tyr14 and Tyr15, whereas Cdc25 dephosphorylates and activates these tyrosine residues. Wee1 or Cdc25 undergoes activation or suppression by the G2/M checkpoint mechanisms. Specifically, the transition from the G2-phase to the M-phase is controlled by the balance between the functions of these enzymes Wee1 and Cdc25 located downstream of the checkpoint.

From the aforementioned functions of Wee1, it is considered that the inhibition of Wee1 can cause the transition of abnormal or defective cells to the M-phase, leading to immature mitosis or cell death. The application of Wee1 inhibitors to anticancer treatment has therefore been deliberated. In fact, a Wee1 inhibitor MK-1775 has been reported to have an anticancer effect (see Non-Patent Document 6). Its anticancer effect or selectivity for cancer cells, however, is less than satisfactory.

On the other hand, a Wee1 inhibitor MK-1775 developed by Merck KGaA has been reported to enhance the cytotoxic effect of a DNA-damaging agent such as gemcitabine on human sarcoma (Non-Patent Document 7). Unlike the DNA-damaging agent such as gemcitabine, Cdc7 inhibitors do not directly cause DNA damage. Hence, no conventional technique has disclosed the combination of a Cdc7 inhibitor and a Wee1 inhibitor or reported its anticancer effect on cancer cells or cancer cell selectivity.

PRIOR ART DOCUMENTS

Patent Documents

[Patent Document 1] International Publication No. WO 2008/046982
[Patent Document 2] International Publication No. WO 2012/133802

Non-Patent Document

[Non-Patent Document 1] H. Masai et al., Journal of Cellular Physiology, 190, 2002, 287-296
[Non-Patent Document 2] D. Bonte et al., Neoplasia, 10, 2008, 920-931
[Non-Patent Document 3] S. Rodriguez-Acebes et al., The American Journal of Pathology, 177, 2010, 2034-2045
[Non-Patent Document 4] A. Montagnoli et al., Cancer Research, 64, 2004, 7110-7116
[Non-Patent Document 5] Masai et al., PLoS One (2012), 7 (5), e36372
[Non-Patent Document 6] A. D. Guertin et al., Molecular Cancer Therapeutics (2013), 12 (8), 1442-1452
[Non-Patent Document 7] J. M. Kreahling et al., PLoS One (2013), 8 (3), e57523

SUMMARY OF INVENTION

Problems to be Solved by the Invention

An object of the present invention is to provide an anticancer composition (combination drug) that induces cell death selectively and specifically for only cancer cells through the control of DNA replication and cell cycle checkpoint mechanisms.

Means of Solving the Problems

The present invention relates to an anticancer composition comprising a Cdc7 inhibitor and an M-phase promoter in combination. More specifically, the present invention relates to the following:
(1) A pharmaceutical composition comprising a Cdc7 inhibitor and an M-phase promoter.
(2) The pharmaceutical composition according to (1), wherein the Cdc7 inhibitor is a furanone derivative represented by the following formula (I):

[Chemical Formula 1]

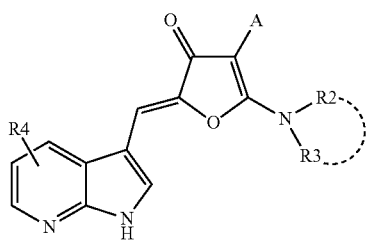

(I)

wherein A represents —COOR1 or a hydrogen atom; R1 represents a hydrogen atom, a hydrocarbon group optionally having a substituent, or a heterocyclic ring optionally having a substituent; R2 and R3 are the same or different and each represent a hydrogen atom, a hydrocarbon group optionally having a substituent, a phenyl group optionally having a substituent, a heterocyclic ring optionally having a substituent, a heterocyclic fused ring optionally having a substituent, or an amino group optionally having a substituent, or R2 and R3 optionally form a heterocyclic ring optionally having a substituent or a heterocyclic fused ring optionally having a substituent, together with the nitrogen atom bonded thereto; and R4 represents a hydrogen atom or a halogen atom, provided that when A represents —COOR1, R2 and R3 do not represent the amino group optionally having a substituent at the same time, and when A represents a hydrogen atom, R3 represents a hydrogen atom, or a pharmaceutically acceptable salt thereof.
(3) The pharmaceutical composition according to (2), wherein the A is —COOR1.
(4) The pharmaceutical composition according to (2), wherein the A is a hydrogen atom.
(5) The pharmaceutical composition according to (3), wherein the furanone derivative has the structure of the following compound (I-A), compound (I-B), compound (I-C), compound (I-D), or compound (I-E):
formula (I-A): isopropyl 5-[(1H-pyrrolo[2,3-b]pyridin-3-yl) methylene]-2-(morpholinoamino)-4-oxo-4,5-dihydrofuran-3-carboxylate

[Chemical Formula 2]

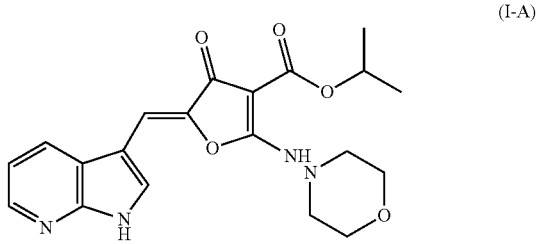

(I-A)

formula (I-B): ethyl 5-[(1H-pyrrolo[2,3-b]pyridin-3-yl) methylene]-2-(7-methoxy-3,4-dihydroisoquinolin-2(1H)-yl)-4-oxo-4,5-dihydrofuran-3-carboxylate

[Chemical Formula 3]

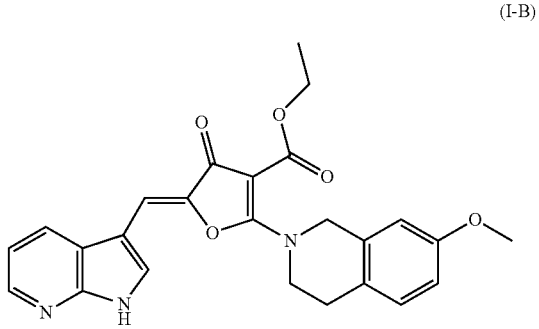

(I-B)

formula (I-C): isopropyl 5-[(1H-pyrrolo[2,3-b]pyridin-3-yl) methylene]-4-oxo-2-{[4-(2,2,2-trifluoroethyl)piperazinyl]amino}-4,5-dihydrofuran-3-carboxylate

[Chemical Formula 4]

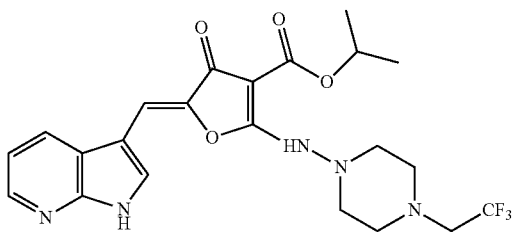

(I-C)

formula (I-D): ethyl 5-[(1H-pyrrolo[2,3-b]pyridin-3-yl)methylene]-4-oxo-2-{[4-(2,2,2-trifluoroethyl)piperazinyl]amino}-4,5-dihydrofuran-3-carboxylate

[Chemical Formula 5]

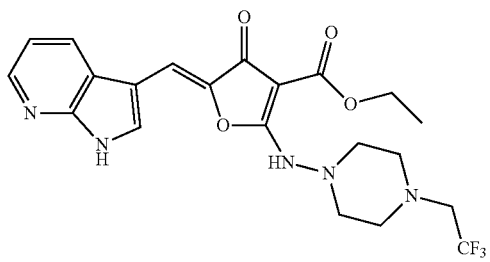

(I-D)

and formula (I-E): cyclopropylmethyl 5-[(1H-pyrrolo[2,3-b]pyridin-3-yl)methylene]-2-(morpholinoamino)-4-oxo-4,5-dihydrofuran-3-carboxylate

[Chemical Formula 6]

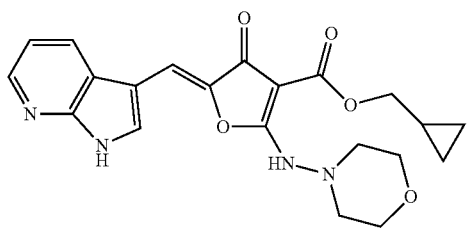

(I-E)

(6) The pharmaceutical composition according to (1), wherein the Cdc7 inhibitor is any of the following compounds:

formula (I-F): 2-(pyridin-4-yl)-1,5,6,7-tetrahydro-4H-pyrrolo[3,2-c]pyridinone

[Chemical Formula 7]

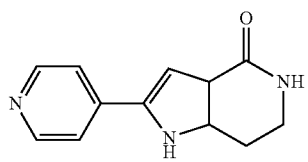

(I-F)

and formula (I-G): 5-(2-amino-pyrimidin-4-yl)-2-(2,4-dichlorophenyl)-1H-pyrrole-3-carboxylic acid amide

[Chemical Formula 8]

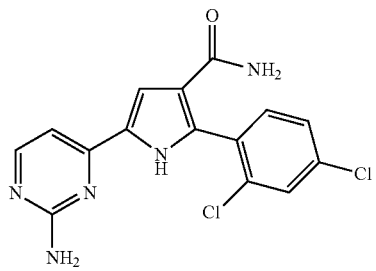

(I-G)

(7) The pharmaceutical composition according to any one of (1) to (6), wherein the M-phase promoter is a Wee1 inhibitor.

(8) The pharmaceutical composition according to (7), wherein the Wee1 inhibitor is MK-1775

[Chemical Formula 9]

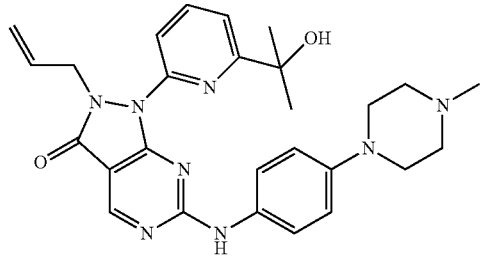

miR-424, miR-381,
6-butyl-4-(2-chlorophenyl)-9-hydroxypyrrolo[3,4-c]carbazole-1,3-(2H,6H)-dione,
9-methoxy-4-(2-methoxy-5-nitrophenyl)-4,5,6,10c-tetrahydropyrrolo[3,4-c]carbazole-1,3(2H,3aH)-dione,
N-[3-(4-(2-chlorophenyl)-9-hydroxy-1,3-dioxo-2,3-dihydropyrrolo[3,4-c]carbazol-6(1H)-yl)propanoyl]benzenesulfonamide,
4-(2,6-dichlorophenyl)-9-hydroxy-6-(3-hydroxypropyl)pyrrolo[3,4-c]carbazole-1,3(2H,6H)-dione,
4-(2,6-dichlorophenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-(1H)-yl)-N-(1H-tetrazol-5-yl)propanamide,
4-(2-chlorophenyl)-9-hydroxy-6-[2-(1H-1,2,4-triazol-5-ylsulfinyl)ethyl]pyrrolo[3,4-c]carbazole-1,3(2H,6H)-dione,
6-(3-bromopropyl)-4-(2-chlorophenyl)-9-hydroxypyrrolo[3,4-c]carbazole-1,3(2H,6H)-dione, 3-(4-(2-chlorophenyl)-9-hydroxy-1,3-dioxo-2,3-dihydropyrrolo[3,4-c]carbazol-6(1H)-yl)propanoic acid,
N-[3-(4-(2-chlorophenyl)-9-hydroxy-1,3-dioxo-2,3-dihydropyrrolo[3,4-c]carbazol-6(1H)-yl)propanoyl]-2-(dimethylamino)ethanesulfonamide,
4-(2-chlorophenyl)-9-hydroxypyrrolo[3,4-c]carbazole-1,3(2H,6H)-dione,
N-[3-(4-(2-chlorophenyl)-9-hydroxy-1,3-dioxo-2,3-dihydropyrrolo[3,4-c]carbazol-6(1H)-yl)propanoyl]methanesulfonamide,
4'-(4-(2-chlorophenyl)-9-hydroxy-1,3-dioxo-2,3-dihydropyrrolo[3,4-c]carbazol-6(1H)-yl)butanoic acid,
N-[4-(4-(2-chlorophenyl)-9-hydroxy-1,3-dioxo-2,3-dihydropyrrolo[3,4-c]carbazol-6(1H)-yl)butanoyl]methanesulfonamide,
6-acetyl-4-(2-chlorophenyl)-9-hydroxypyrrolo[3,4-c]carbazole-1,3(2H,6H)-dione,
3-(4-(2,6-dichlorophenyl)-9-hydroxy-1,3-dioxo-2,3-dihydropyrrolo[3,4-c]carbazol-6(1H)-yl)-N-[2-(dimethylamino)ethyl]propanamide,
3-(4-(2-chlorophenyl)-9-hydroxy-1,3-dioxo-2,3-dihydropyrrolo[3,4-c]carbazol-6(1H)-yl)propanenitrile,
4-(2-chlorophenyl)-9-hydroxy-6-[3-(1H-tetrazol-5-yl)propyl]pyrrolo[3,4-c]carbazole-1,3(2H,6H)-dione,
4-(2-chlorophenyl))-9-hydroxy-6-[2-(1H-imidazol-2-ylsulfanyl)ethyl]pyrrolo[3,4-c]carbazole-1,3(2H,6H)-dione,
N-[4-(4-(2-chlorophenyl)-9-hydroxy-1,3-dioxo-2,3-dihydropyrrolo[3,4-c]carbazol-6(1H)-yl)butanoyl]benzenesulfonamide,
4-(2-chlorophenyl)-9-hydroxy-6-[2-(1H-1,2,4-triazol-5-ylsulfonyl)ethyl]pyrrolo[3,4-c]carbazole-1,3(2H,6H)-dione,
4-(2-chlorophenyl)-9-hydroxy-6-[2-(1H-imidazol-2-ylsulfinyl)ethyl]pyrrolo[3,4-c]carbazole-1,3(2H,6H)-dione,
4-(2-chlorophenyl)-9-hydroxy-6-[2-(1H-tetrazol-5-yl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanamide,
4-(2-chlorophenyl)-9-hydroxy-6-[2-(1H-imidazol-2-ylsulfonyl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanoic acid,
4-(2-chlorophenyl)-6-(2,3-dihydroxypropyl)-9-hydroxypyrrolo[3,4-c]carbazole-1,3(2H,6H)-dione,
2-(4-(2,6-dichlorophenyl)-9-hydroxy-1,3-dioxo-2,3-dihydropyrrolo[3,4-c]carbazol-6(1H)-yl)ethylmethanesulfonate,
4-(2-chlorophenyl)-9-hydroxy-6-[2-(4H-1,2,4-triazol-3-ylsulfanyl)ethyl]pyrrolo[3,4-c]carbazole-1,3(2H,6H)-dione,
9-hydroxy-6-(2-hydroxyethyl)-4-phenylpyrrolo[3,4-c]carbazole-1,3(2H,6H)-dione,
6-(3-bromopropyl)-4-(2,6-dichlorophenyl)-9-hydroxypyrrolo[3,4-c]carbazole-1,3(2H,6H)-dione,
4-(2-chlorophenyl)-9-hydroxy-6-(3-methoxypropyl)pyrrolo[3,4-c]carbazole-1,3(2H,6H)-dione,
4-(2-chlorophenyl)-9-hydroxy-6-(2-hydroxypropyl)pyrrolo[3,4-c]carbazole-1,3(2H,6H)-dione,
4-(2-chlorophenyl)-9-hydroxy-6-[(2S)-3-hydroxy-2-methylpropyl]pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(1H-imidazol-5-yl)ethyl]propanamide,
9-hydroxy-6-(3-hydroxypropyl)-4-(2-methoxyphenyl)pyrrolo[3,4-c]carbazole-1,3(2H,6H)-dione,
methyl 3-(4-(2-chlorophenyl)-9-hydroxy-1,3-dioxo-2,3-dihydropyrrolo[3,4-c]carbazol-6(1H)-yl)propanoate,
3-(4-(2-chlorophenyl)-9-hydroxy-1,3-dioxo-2,3-dihydropyrrolo[3,4-c]carbazol-6(1H)-yl)-N-[2-(4-morpholinyl)ethyl]propanamide,
4-(4-(2-chlorophenyl)-9-hydroxy-1,3-dioxo-2,3-dihydropyrrolo[3,4-c]carbazol-6(1H)-yl]butanenitrile,
4-(2-chloro-6-methoxyphenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-6-(3,4-dihydroxybutyl)-9-hydroxypyrrolo[3,4-c]carbazole-1,3(2H,6H)-dione,
3-(4-(2-chloro-6-methoxyphenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-9-hydroxy-6-[(2R)-3-hydroxy-2-methylpropyl]pyrrolo[3,4-c]carbazole-1,3(2H,6H)-dione,
2-(4-(2-chlorophenyl)-9-hydroxy-1,3-dioxo-2,3-dihydropyrrolo[3,4-c]carbazol-6(1H)-yl)ethylmethanesulfonate,
4-(2-chloro-6-methoxyphenyl)-9-hydroxy-6-(3-hydroxypropyl)pyrrolo[3,4-c]carbazole-1,3(2H,6H)-dione,
9-hydroxy-6-(2-hydroxyethyl)-4-(2-methoxyphenyl)pyrrolo[3,4-c]carbazole-1,3(2H,6H)-dione,
4-(2-chlorophenyl)-6-(2-hydroxyethyl)-9-hydroxypyrrolo[3,4-c]carbazole-1,3(2H,6H)-dione,
4-(2-chlorophenyl)-9-hydroxy-6-[3-(methyl sulfanyl)propyl]pyrrolo[3,4-c]carbazole-1,3(2H,6H)-dione,
4-(2-chlorophenyl)-6-ethyl-9-hydroxypyrrolo[3,4-c]carbazole-1,3(2H,6H)-dione,
4-(2-chlorophenyl)-9-hydroxy-6-isopropylpyrrolo[3,4-c]carbazole-1,3(2H,6H)-dione,
4-(2-chlorophenyl)-9-hydroxy-6-[3-(1H-imidazol-1-yl)propyl]pyrrolo[3,4-c]carbazole-1,3(2H,6H)-dione,
4-(2-chloro-6-methoxyphenyl)-9-hydroxy-6-[3-(4-morpholinyl)propyl]pyrrolo[3,4-c]carbazole-1,3(2H,6H)-dione,
6-(2-chloroethyl)-4-(2-chlorophenyl)-9-hydroxypyrrolo[3,4-c]carbazole-1,3(2H,6H)-dione,
6-(3-bromopropyl)-4-(2-chloro-6-methoxyphenyl)-9-hydroxypyrrolo[3,4-c]carbazole-1,3(2H,6H)-dione,
4-(2-chlorophenyl)-9-hydroxy-6-[2-hydroxy-3-(methylamino)propyl]pyrrolo[3,4-c]carbazole-1,3(2H,6H)-dione,
4-(2-chlorophenyl)-9-hydroxy-6-methylpyrrolo[3,4-c]carbazole-1,3(2H,6H)-dione,
4-(2-chlorophenyl)-9-hydroxy-6-[2-hydroxy-3-(4-morpholinyl)propyl]pyrrolo[3,4-c]carbazole-1,3(2H,6H)-dione, or
4-(2,6-dichlorophenyl)-9-hydroxy-6-[3-(1H-imidazol-1-yl)propyl]pyrrolo[3,4-c]carbazole-1,3(2H,6H)-dione.

(9) The pharmaceutical composition according to any one of (1) to (6), wherein the M-phase promoter is a Chk1 inhibitor, an Hsp90 inhibitor, or a Myt1 inhibitor.

(10) The pharmaceutical composition according to (9), wherein the Chk1 inhibitor is SCH900776, UCN-01, GDC-0425, XL844, CEP-3891, CHIR-124, CHIR-600, PF-00394691, PF-00477736, N-aryl-N'-pyrazinylurea, Go6976, SB-218078, ICP-1, PD-0166285, CBP-501, staurosporine, isogranulatimide, debromohymenialdisine (DBH), scytonemin, pyrimidine, pyrrolopyrimidine, pyrazolopyrimidine, furanopyrimidine, pyrazoloquinoline, imidazopyrazine, pyrimidinylindazolylamine, 2-ureidothiophene, 3-ureidothiophene, triazolone, diarylurea, benzimidazole quinolone, dibenzodiazepinone, indolinone, aminopyrazole, indenopyrazole, or diazepinoindolone.

(11) The pharmaceutical composition according to (9), wherein the Hsp90 inhibitor is geldanamycin, tanespimycin (17-AAG), 17-aminodemethoxygeldanamycin (IPI-493), 17-dimethylaminoethylamino-17-demethoxygeldanamycin (17-DMAG), XL888, SNX-2112, SNX-5422, SNX-7081, ganetespib (STA-9090), AT13387, AUY922, Debio0932, BIIB028, BIIB021, MPC-3100, MPC-0767, retaspimycin (IPI-504), PU3, PU24FCI, PU-H58, PU-H71, DS-2248, KW-2478, CCT018159, CCT0129397, BJ-B11, elesclomol (STA-4783), G3130, gedunin, herbimycin, radester, KNK437, HSP990, or NVP-BEP800.

(12) The pharmaceutical composition according to (9), wherein the Myt1 inhibitor is
2-(4-fluorophenylamino)-4-(4-pyridyl)thiazole,
2-(4-fluorophenylamino)-4-(4-fluorophenyl)thiazole,
3-(3,4-dichlorophenyl)-5-[4-[2-[(2-pyridyl)amino]thiazolyl]]-isoxazole,
3-(3,4-dichlorophenyl)-5-[4-[2-(3-pyridyl)amino]thiazolyl]-isoxazole,
1,4-bis(2-phenylamino-4-thiazolyl)benzene,
1,4-bis(2-phenylamino-4-thiazolyl)benzene dihydrobromide,
1-[2-phenyl-4-(5-bromo)thiazolyl]-4-[2-phenyl-4-thiazolyl]benzene,
1-[2-phenyl-4-(5-bromo)thiazolyl]-4-[2-phenyl-4-thiazolyl]benzene dihydrobromide,
1,4-bis(2-phenyl)-(4-(5-bromo)thiazolylbenzene,
1,4-bis(2-phenyl)-(4-(5-bromo)thiazolylbenzene dihydrobromide,
1,4-bis(2-(3-pyridylamino)-4-thiazolyl)benzene,
1,4-bis(2-(3-pyridylamino)-4-thiazolyl)benzene bistrifluoroacetate,
1-[(2-(3-pyridylamino)-4-(5-bromo)thiazolyl)]-4-[2-(3-pyridylamino)-4-thiazolyl]benzene,
1-[(2-(3-pyridylamino)-4-(5-bromo)thiazolyl)]-4-[2-(3-pyridylamino)-4-thiazolyl]benzene bistrifluoroacetate,
1,3-bis(2-(3-pyridylamino)-4-thiazolyl)benzene,
1,3-bis(2-(3-pyridylamino)-4-thiazolyl)benzene dihydrobromide,
1,4-bis(2-(2-pyridylamino)-4-thiazolyl)benzene,
1,4-bis(2-(2-pyridylamino)-4-thiazolyl)benzene dihydrobromide,
1,3-bis(2-(2-pyridylamino)-4-thiazolyl)benzene,
1,3-bis(2-(2-pyridylamino)-4-thiazolyl)benzene dihydrobromide,
4,4'-di(2,2-phenylaminothiazolyl),
4,4'-di(2,2-phenylaminothiazolyl) dihydrobromide,
4,4'-di(2-(2-methoxypyrid-5-ylamino)thiazolyl),
4,4'-di(2-(2-methoxypyrid-5-ylamino)thiazolyl) bistrifluoroacetate,
4,4'-di(2-(2-pyridyl)aminothiazolyl),
4,4'-di(2-(2-pyridyl)aminothiazolyl) bistrifluoroacetate,
bis[2-(4-phenyl-5-methyl)thiazolyl]amine,
bis[2-(4-phenyl-5-methyl)thiazolyl]amine hydrobromide,
bis[2-(4-(2-pyridyl)thiazolyl]amine,
bis[2-(4-(2-pyridyl)thiazolyl]amine dihydrobromide,
bis[2-[4-(3-pyridyl)thiazolyl)amine,
bis[2-[4-(3-pyridyl)thiazolyl)amine bistrifluoroacetate,
N,N-bis(5(3,4-dichlorophenyl)-2-thiazolyl)amine,
N,N-bis(5(3,4-dichlorophenyl)-2-thiazolyl)amine dihydrobromide,
1,3-bis[4-(3-pyridyl)-2-thiazolylamino]benzene,
1,3-bis[4-(3-pyridyl)-2-thiazolylamino]benzene dihydrobromide, or dasatinib.

(13) An anticancer composition comprising a pharmaceutical composition according to any one of (1) to (12).

(14) A therapeutic drug for cancer comprising a Cdc7 inhibitor and an M-phase promoter in combination.

(15) The therapeutic drug for cancer according to (14), wherein the therapeutic drug for cancer is a combination drug.

(16) The therapeutic drug for cancer according to (14), wherein the therapeutic drug for cancer is a kit comprising a drug containing the Cdc7 inhibitor and a drug containing the M-phase promoter.

Effect of the Invention

The combination of a Cdc7 inhibitor and an M-phase promoter can bring about cell death more efficiently with higher selectivity and specificity for a wide range of cancer cells, as compared with use of the Cdc7 inhibitor or the M-phase promoter alone. Particularly, the Cdc7 inhibitor can maintain cell survival by leading cancer cells to cell death while safely arresting the cell cycle of normal cells. On the other hand, the M-phase promoter causes the accumulation of DNA damage and the induction of mitotic-phase cell death by promoting abnormal progression to the M-phase through the invalidation of the cell cycle checkpoints of cancer cells. Such an anticancer agent has the new mechanism of action.

BRIEF DESCRIPTION OF THE DRAWINGS

FIG. 1 is a diagram of FACS showing the interaction between compound (I-D) or compound (I-E) as a Cdc7 inhibitor and a Wee1 inhibitor (MK-1775) as an M-phase promoter for colon cancer cells.

FIG. 2 is a diagram of FACS showing the interaction between compound (I-D) or compound (I-E) and a Wee1 inhibitor (MK-1775) for normal cells.

FIG. 3 is a diagram of FACS showing the interaction between compound (I-D) or compound (I-E) and MK-1775 for Panc-1 cells (pancreatic cancer cell line).

FIG. 4 is a diagram of FACS showing that a combination drug of compound (I-D) or compound (I-E) and MK-1775 is effective even if its composition is changed.

FIG. 5 is a diagram of FACS showing the interaction between compound (I-A) as a Cdc7 inhibitor and MK-1775 in combination.

FIG. 6 is a diagram of FACS showing the interaction between compound (I-B) as a Cdc7 inhibitor and MK-1775 in combination.

FIG. 7 is a diagram of FACS showing the interaction between compound (I-C) as a Cdc7 inhibitor and MK-1775 in combination.

FIG. 8 is a diagram of FACS showing the interaction between a Cdc7 inhibitor (compound (I-F) or compound (I-G)) and MK-1775 in combination.

FIG. 9 is a diagram of FACS showing the interaction between a Chk1 inhibitor SCH900776 (SCH) as an M-phase promoter and compound (I-D) or compound (I-E) in combination.

FIG. 10 is a diagram of FACS showing the interaction between a kinase (e.g., Chk1) inhibitor UCN-01 as an M-phase promoter and compound (I-D) or compound (I-E) in combination.

FIG. 11 is a diagram of FACS showing the interaction between an Hsp90 inhibitor geldanamycin as an M-phase promoter and compound (I-D) or compound (I-E) in combination.

FIG. 12 is a diagram of the rate of inhibition of cell growth showing the interaction between compound (I-D) and a Wee1 inhibitor (MK-1775) in combination for human breast cancer cells (MDA-MB-231).

FIG. 13 is a diagram of the rate of inhibition of cell growth showing the interaction between compound (I-E) and a Wee1 inhibitor (MK-1775) in combination for human breast cancer cells (MDA-MB-231).

FIG. 14 is a diagram of BLISS scores showing the interaction between compound (I-D) and a Wee1 inhibitor (MK-1775) in combination for human breast cancer cells (MDA-MB-231).

FIG. 15 is a diagram of BLISS scores showing the interaction between compound (I-E) and a Wee1 inhibitor (MK-1775) in combination for human breast cancer cells (MDA-MB-231).

DESCRIPTION OF EMBODIMENTS (1) Cdc7 Inhibitor

In the present invention, the Cdc7 inhibitor refers to a drug that inhibits Cdc7 kinase activity and includes drugs inhibiting Cdc7 kinase, such as low-molecular compounds, polypeptides, proteins, nucleic acids (siRNA, miRNA, aptamers, etc.), and other high-molecular compounds.

The inhibition of Cdc7 allows abnormal DNA replication specific for cancer cells to proceed to induce cell death. In normal cells, the normal DNA replication checkpoint mechanism works to arrest the cell cycle so that the survival thereof can be maintained. More specifically, Cdc7 causes the phosphorylation of the MCM protein in a complex before DNA replication and promotes replication origin firing.

The inhibition of Cdc7 inhibits replication origin firing and therefore decreases the replication origin to stall replication forks, resulting in an incomplete replication state. In the presence of a cancerous gene mutation that influences the DNA replication checkpoint, the cell cycle proceeds abnormally so that DNA damage is induced in the M-phase to cause the accumulation of the DNA damage. Finally, cell death specific for cancer cells is induced.

Examples of the Cdc7 inhibitor include compounds listed in JP 2013-525354 A, JP 2013-525304 A, JP 2013-525303 A, JP 2013-522212 A, JP 2013-511487 A, JP 2012-533553 A, JP 2012-533551 A, JP 2012-519653 A, JP 2011-507908 A, JP 2010-527324 A, JP 2010-519324 A, JP 2010-505922 A, JP 2009-534400 A, JP 2009-531373 A (International Publication No. WO 2007/110344), JP 2009-519919 A, JP 2009-515849 A, JP 2007-501827 A, JP 2007-501825 A, Domestic Re-publication of PCT International Publication for Patent Application Nos. 2011/102399 and 2010/122979, and International Publication Nos. WO 2011/102399, WO 2012/002568, and WO 2012/133802 (Patent Document 2).

According to one embodiment, the Cdc7 inhibitor is a furanone derivative represented by the following formula (I):

[Chemical Formula 10]

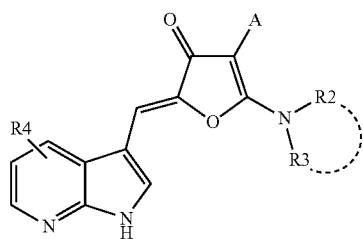

wherein A represents —COOR1 or a hydrogen atom; R1 represents a hydrogen atom, a hydrocarbon group optionally having a substituent, or a heterocyclic ring optionally having a substituent; R2 and R3 are the same or different and each represent a hydrogen atom, a hydrocarbon group optionally having a substituent, a phenyl group optionally having a substituent, a heterocyclic ring optionally having a substituent, a heterocyclic fused ring optionally having a substituent, or an amino group optionally having a substituent, or R2 and R3 optionally form a heterocyclic ring optionally having a substituent or a heterocyclic fused ring optionally having a substituent, together with the nitrogen atom bonded thereto; and R4 represents a hydrogen atom or a halogen atom, provided that when A represents —COOR1, R2 and R3 do not represent the amino group optionally having a substituent at the same time, and when A represents a hydrogen atom, R3 represents a hydrogen atom, or a pharmaceutically acceptable salt thereof, which is described in International Publication No. WO 2012/133802 (Patent Document 2).

In the formula (I), examples of the hydrocarbon group optionally having a substituent include
a) a linear or branched alkyl group having 1 to 6 carbon atoms (e.g., methyl, ethyl, isopropyl, tert-butyl, and hexyl), b) a linear or branched alkenyl group having 1 to 6 carbon atoms (e.g., vinyl, allyl, isopropenyl, and 2-butenyl), c) an alkynyl group having 2 to 6 carbon atoms (e.g., ethynyl, propargyl, and 2-butynyl), d) a cycloalkyl group having 3 to 8 carbon atoms (e.g., cyclopropyl, cyclopentyl, cyclohexyl, and cycloheptyl), e) a cycloalkenyl group having 3 to 8 carbon atoms (e.g., cyclohexenyl and cycloheptenyl), and f) an aralkyl group whose aryl moiety is aryl having 6 to 14 carbon atoms (e.g., phenyl, naphthyl, and indenyl) and whose alkylene moiety is a group in which one hydrogen atom has been removed from the alkyl group.

Examples of the heterocyclic moiety of the heterocyclic ring optionally having a substituent include an alicyclic heterocyclic group and an aromatic heterocyclic group. Examples of the alicyclic heterocyclic group include a 3- to 8-membered heterocyclic group containing at least one heteroatom selected from a nitrogen atom, a sulfur atom, and an oxygen atom. Specific examples thereof include pyrrolidinyl, piperidyl, piperazinyl, morpholinyl, and thiomorpholinyl. Examples of the aromatic heterocyclic group include a 5- or 6-membered monocyclic aromatic heterocyclic group containing at least one heteroatom selected from a nitrogen atom, a sulfur atom, and an oxygen atom. Specific examples thereof include imidazolyl, pyrazolyl, thienyl, thiazolyl, and pyridyl.

Examples of the heterocyclic fused ring moiety of the heterocyclic fused ring optionally having a substituent include a 3- to 8-membered ring-fused bicyclic heterocyclic group containing at least one heteroatom selected from a nitrogen atom, a sulfur atom, and an oxygen atom. Specific examples thereof include benzothiophenyl, benzimidazolyl, indazolyl, benzoxazolyl, benzothiazolyl, indolyl, isoquinolyl, and phthalimide.

Examples of the amino group optionally having a substituent include an amino group having a linear, branched, or cyclic alkyl group having 1 to 6 carbon atoms, an aryl group, a heteroaryl group, or the like which is substituted or unsubstituted and include an amino group bonded to an alkyl group, an alkylamino group, an aryl group, a heteroaryl group, a heterocyclic group, a heterocyclic fused ring group, or the like which has one or two or more substituents or is unsubstituted. The "one or two or more substituents" in these groups bonded to an amino group may be one or two or more identical or different arbitrary groups, unless otherwise specified. Examples thereof include a halogen atom, a substituted or unsubstituted alkyl group, a substituted or unsubstituted alkenyl group, a substituted or unsubstituted alkynyl group, a substituted or unsubstituted alkoxy group, an amino group, a nitro group, a cyano group, a hydroxy group, a substituted or unsubstituted alkylamino group, a carbamoyl group, a carboxyl group, a formyl group, an acetyl group, and a benzoyl group.

The "substituent" in the hydrocarbon group optionally having a substituent, the heterocyclic ring optionally having a substituent, the phenyl group optionally having a substituent, or the heterocyclic fused ring optionally having a substituent may be one or two or more arbitrary types of substituents that are located at arbitrary chemically possible positions, unless otherwise specified. In the case of two or more substituents, these substituents may be the same as or different from each other. Examples thereof include a halogen atom, a substituted or unsubstituted alkyl group, a substituted or unsubstituted alkoxy group, a substituted or unsubstituted amino group, a nitro group, a cyano group, a hydroxy group, a substituted or unsubstituted alkylamino group, a carbamoyl group, a carboxyl group, a formyl group, an acetyl group, and a benzoyl group.

Examples of the heterocyclic group in the heterocyclic ring optionally having a substituent or the heterocyclic fused ring optionally having a substituent which is formed by R2 and R3 together with the nitrogen atom bonded thereto include a 3- to 8-membered heterocyclic group containing at least one heteroatom selected from a nitrogen atom, a sulfur atom, and an oxygen atom or a 3- to 8-membered ring-fused bicyclic alicyclic heterocyclic group containing at least one heteroatom selected from a nitrogen atom, a sulfur atom, and an oxygen atom and specifically include pyrrolidinyl, piperidyl, morpholinyl, thiomorpholinyl, azepinyl, diazepinyl, dihydroisoquinolyl, tetrahydroisoquinolyl, tetrahydroquinolyl, isoindolinyl, indolinyl, tetrahydrobenzazepinyl, benzazepinyl, benzodiazepinyl, benzoxazepinyl, and benzothiazepinyl. Examples of the halogen atom include fluorine, chlorine, and bromine.

The compound (I) according to the present invention may include isomers, for example, depending on the types of substituents. In the present specification, these isomers may be indicated by only one form of a chemical structure. The present invention also encompasses all structurally possible isomers (geometric isomers, optical isomers, tautomers, etc.) and encompasses isomers alone and mixtures thereof. The present invention also encompasses these stereoisomers specifically represented by the formulas (Z)-(I) and (E)-(I) as the compounds according to the present invention, and mixtures thereof.

[Chemical Formula 11]

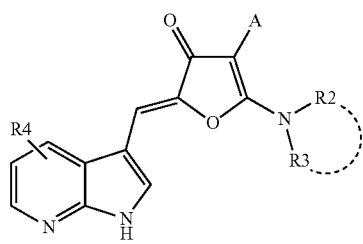

(Z)-(I)

-continued

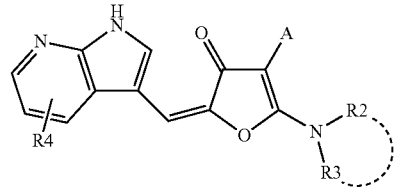

(E)-(I)

Examples of the pharmaceutically acceptable salt of the compound (I) according to the present invention include: salts of inorganic acids such as hydrochloric acid, sulfuric acid, carbonic acid, and phosphoric acid; and salts of organic acids such as formic acid, acetic acid, fumaric acid, maleic acid, methanesulfonic acid, and p-toluenesulfonic acid. The present invention also encompasses: salts of alkali metals such as sodium and potassium; salts of alkaline earth metals such as magnesium and calcium; salts of organic amines such as lower alkylamine and lower alcohol amine; salts of basic amino acids such as lysine, arginine, and ornithine; and other salts such as ammonium salt.

The compound (I) according to the present invention and the pharmaceutically acceptable salt thereof can be produced by a method described in, for example, International Publication No. WO 2012/133802. In the production method described in International Publication No. WO 2012/133802, the defined groups may vary under conditions of the implemented method or may be inappropriate for carrying out the method. In such a case, the compound (I) according to the present invention and the pharmaceutically acceptable salt thereof can be readily produced by a method usually used in organic synthetic chemistry, for example, approaches of the protection and deprotection of functional groups [T. W. Greene, Protective Groups in Organic Synthesis 3rd Edition, John Wiley & Sons, Inc., 1999]. If necessary, the order of reaction steps including the introduction of substituents may be changed.

The compound of the formula (I) is preferably a compound wherein A is —COOR1 or a hydrogen atom and more preferably has the structure of the following compound (I-A), compound (I-B), compound (I-C), compound (I-D), or compound (I-E).

formula (I-A): isopropyl 5-[(1H-pyrrolo[2,3-b]pyridin-3-yl)methylene]-2-(morpholinoamino)-4-oxo-4,5-dihydrofuran-3-carboxylate

[Chemical Formula 12]

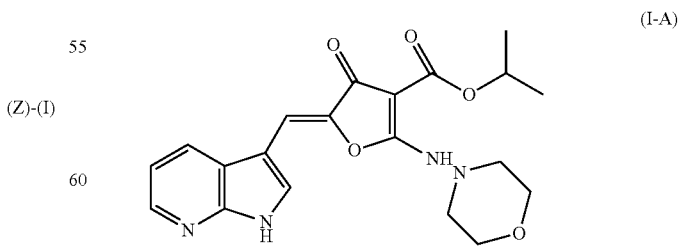

(I-A)

compound (I-B): ethyl 5-[(1H-pyrrolo[2,3-b]pyridin-3-yl)methylene]-2-(7-methoxy-3,4-dihydroisoquinolin-2(1H)-yl)-4-oxo-4,5-dihydrofuran-3-carboxylate

[Chemical Formula 13]

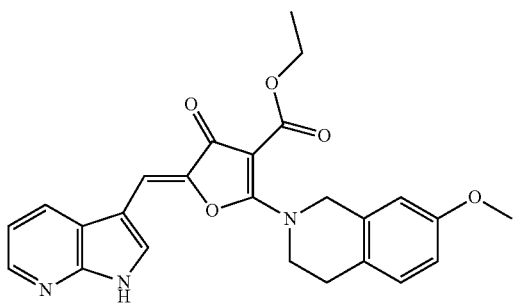

(I-B)

compound (I-C): isopropyl 5-[(1H-pyrrolo[2,3-b]pyridin-3-yl)methylene]-4-oxo-2-{[4-(2,2,2-trifluoroethyl)piperazinyl]amino}-4,5-dihydrofuran-3-carboxylate

[Chemical Formula 14]

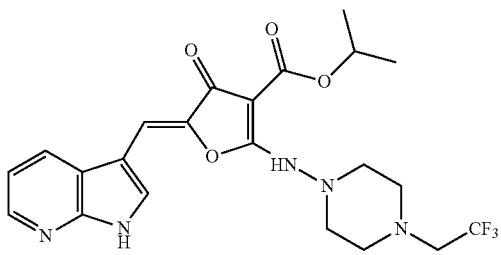

(I-C)

compound (I-D): ethyl 5-[(1H-pyrrolo[2,3-b]pyridin-3-yl)methylene]-4-oxo-2-{[4-(2,2,2-trifluoroethyl)piperazinyl]amino}-4,5-dihydrofuran-3-carboxylate

[Chemical Formula 15]

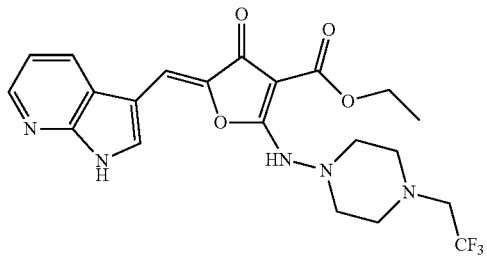

(I-D)

and compound (I-E): cyclopropylmethyl 5-[(1H-pyrrolo[2,3-b]pyridin-3-yl)methylene]-2-(morpholinoamino)-4-oxo-4,5-dihydrofuran-3-carboxylate

[Chemical Formula 16]

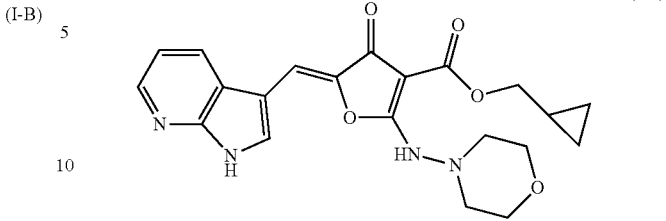

(I-E)

In this context, the compound (I-A) is a compound of Example 245 in the specification of Patent Document 2: International Publication No. WO 2012/133802; the compound (I-B) is a compound of Example 244 in the specification of Patent Document 2: International Publication No. WO 2012/133802; the compound (I-C) is a compound of Example 351 in the specification of Patent Document 2: International Publication No. WO 2012/133802; the compound (I-D) is a compound of Example 246 in Patent Document 2: International Publication No. WO 2012/133802; and the compound (I-E) is a compound of Example 347 in Patent Document 2: International Publication No. WO 2012/133802.

According to another embodiment, the Cdc7 inhibitor is compound (I-F): 2-(pyridin-4-yl)-1,5,6,7-tetrahydro-4H-pyrrolo[3,2-c]pyridinone (Merck KGaA, catalog No.: 217707-5MGCN, 217707)

[Chemical Formula 17]

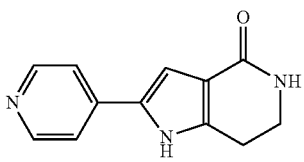

(I-F)

or compound (I-G): 5-(2-amino-pyrimidin-4-yl)-2-(2,4-dichloro-phenyl)-1H-pyrrole-3-carboxylic acid amide (compound F26 in the specifications of JP 2009-531373 A and International Publication No. WO 2007/110344)

[Chemical Formula 18]

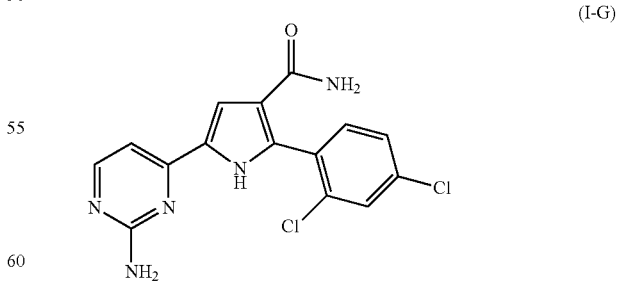

(I-G)

(2) M-Phase Promoter

In the present invention, the M-phase promoter refers to a drug having the function of promoting the process from the transition of cells through the G2/M checkpoint of the cell cycle to the M-phase, which is a mitotic phase.

The G2/M checkpoint is a checkpoint that controls the transition from the G2-phase to the M-phase. Upon activation of this control by DNA damage or the like, the initiation of the M-phase is inhibited so that the cells remain in the G2-phase. In response to DNA damage, ATR (ataxia-telangiectasia mutated related) activated by phosphorylation phosphorylates and activates Chk1. Subsequently, the active form of Chk1 downregulates the phosphorylation of Cdc25 and inhibits the dephosphorylation of Cdk1 by the phosphorylated Cdc25. Cdk1 is therefore kept in a highly phosphorylated and inactive state. Thus, the cell cycle of the cells is arrested without proceeding to the M-phase.

Thus, in the unphosphorylated state of Cdk1, the transition of the cells to the M-phase occurs to promote the cell cycle. A substance that participates in the mechanism of the process from the G2/M checkpoint of the cell cycle to the transition to the M-phase and promotes the transition of cells to the M-phase can be regarded as the M-phase promoter according to the present invention even if the substance is any of low molecules and high molecules such as nucleic acids or proteins.

Examples of the M-phase promoter include a Wee1 inhibitor, a Chk1 inhibitor, a Myt1 inhibitor, and a Cdc25 activator. Further examples thereof include an Hsp90 inhibitor (geldanamycin, Oncogene, 2008; 27: 5567) and a poly (ADP-ribose) glycohydrolase (PARG) inhibitor (Biochem Biophys Res Commun, 2013; 441: 793; and Molecules, 2011; 16: 1854), which have not been reported to participate directly in the G2/M checkpoint, but have been reported to promote the transition from the G2-phase to the M-phase.

In this context, Wee1 is a nuclear kinase that belongs to protein kinases of the Ser/Thr family. Wee1 inhibits Cdk1 through the phosphorylation thereof at Tyr15 and Thr14 sites in the amino acid sequence. This Cdk1 plays an important role in various cyclin-dependent pathways of cell cycle checkpoints.

In the G2/M checkpoint, Wee1 phosphorylates Cdk1 at Tyr15 and Thr14 so that the kinase activity of the Cdk1 is kept low to hinder the transition to the M-phase (mitosis). On the other hand, during the transition to the M-phase, the activity of Wee1 is reduced by some control factors, resulting in enhanced Cdk1 activity.

The DNA damage checkpoint controls the G2/M transition by delaying the transition of cells having DNA damage to the M-phase (mitosis).

Thus, a drug that inhibits the functions of the Wee1 kinase (in the present invention, this drug is referred to as a Wee1 inhibitor) promotes the transition of cells to the M-phase via the G2/M transition. Hence, the Wee1 inhibitor can be a typical example of the M-phase promoter.

MK-1775 represented by the following structural formula:

[Chemical Formula 19]

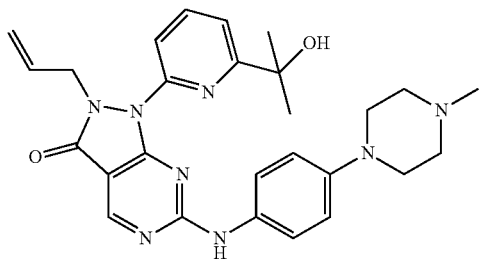

is a potent and selective Wee1 inhibitor having $IC_{50}$ of 5.2 nM and has the function of masking the DNA damage checkpoint. Its application to ovary cancer by combined use with a standard chemical therapy using a DNA-damaging agent has been attempted.

Examples of the Wee1 inhibitor include miR-424, miR-381, and 6-butyl-4-(2-chlorophenyl)-9-hydroxypyrrolo[3,4-c]carbazole-1,3-(2H,6H)-dione,
9-methoxy-4-(2-methoxy-5-nitrophenyl)-4,5,6,10c-tetrahydropyrrolo[3,4-c]carbazole-1,3(2H,3aH)-dione,
N-[3-(4-(2-chlorophenyl)-9-hydroxy-1,3-dioxo-2,3-dihydropyrrolo[3,4-c]carbazol-6(1H)-yl)propanoyl]benzenesulfonamide,
4-(2,6-dichlorophenyl)-9-hydroxy-6-(3-hydroxypropyl)pyrrolo[3,4-c]carbazole-1,3(2H,6H)-dione,
4-(2,6-dichlorophenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-(1H)-yl)-N-(1 H-tetrazol-5-yl)propanamide,
4-(2-chlorophenyl)-9-hydroxy-6-[2-(1H-1,2,4-triazol-5-ylsulfinyl)ethyl]pyrrolo[3,4-c]carbazole-1,3(2H,6H)-dione,
6-(3-bromopropyl)-4-(2-chlorophenyl)-9-hydroxypyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)propanoic acid,
N-[3-(4-(2-chlorophenyl)-9-hydroxy-1,3-dioxo-2,3-dihydropyrrolo[3,4-c]carbazol-6(1H)-yl)propanoyl]-2-(dimethylamino)ethanesulfonamide,
4-(2-chlorophenyl)-9-hydroxypyrrolo[3,4-c]carbazole-1,3(2H,6H)-dione,
N-[3-(4-(2-chlorophenyl)-9-hydroxy-1,3-dioxo-2,3-dihydropyrrolo[3,4-c]carbazol-6(1H)-yl)propanoyl]methanesulfonamide,
4'-(4-(2-chlorophenyl)-9-hydroxy-1,3-dioxo-2,3-dihydropyrrolo[3,4-c]carbazol-6(1H)-yl)butanoic acid,
N-[4-(4-(2-chlorophenyl)-9-hydroxy-1,3-dioxo-2,3-dihydropyrrolo[3,4-c]carbazol-6(1H)-yl)butanoyl]methanesulfonamide,
6-acetyl-4-(2-chlorophenyl)-9-hydroxypyrrolo[3,4-c]carbazole-1,3(2H,6H)-dione,
3-(4-(2, 6-dichlorophenyl)-9-hydroxy-1,3-dioxo-2,3-dihydropyrrolo[3,4-c]carbazol-6(1H)-yl)-N-[2-(dimethylamino)ethyl]propanamide,
3-(4-(2-chlorophenyl)-9-hydroxy-1,3-dioxo-2,3-dihydropyrrolo[3,4-c]carbazol-6(1H)-yl)propanenitrile,
4-(2-chlorophenyl)-9-hydroxy-6-[3-(1H-tetrazol-5-yl)propyl]pyrrolo[3,4-c]carbazole-1,3(2H,6H)-dione,
4-(2-chlorophenyl))-9-hydroxy-6-[2-(1H-imidazol-2-ylsulfanyl)ethyl]pyrrolo[3,4-c]carbazole-1,3(2H,6H)-dione,
N-[4-(4-(2-chlorophenyl)-9-hydroxy-1,3-dioxo-2,3-dihydropyrrolo[3,4-c]carbazol-6(1H)-yl)butanoyl]benzenesulfonamide,
4-(2-chlorophenyl)-9-hydroxy-6-[2-(1H-1,2,4-triazol-5-ylsulfonyl)ethyl]pyrrolo[3,4-c]carbazole-1,3(2H,6H)-dione,
4-(2-chlorophenyl)-9-hydroxy-6-[2-(1H-imidazol-2-ylsulfinyl)ethyl]pyrrolo[3,4-c]carbazole-1,3(2H,6H)-dione,
4-(2-chlorophenyl)-9-hydroxy-6-[2-(1H-tetrazol-5-yl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanamide,
4-(2-chlorophenyl)-9-hydroxy-6-[2-(1H-imidazol-2-ylsulfonyl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanoic acid, 4-(2-chlorophenyl)-6-(2,3-dihydroxypropyl)-9-hydroxypyrrolo[3,4-c]carbazole-1,3(2H,6H)-dione,
2-(4-(2,6-dichlorophenyl)-9-hydroxy-1,3-dioxo-2,3-dihydropyrrolo[3,4-c]carbazol-6(1H)-yl)ethylmethanesulfonate,
4-(2-chlorophenyl)-9-hydroxy-6-[2-(4H-1,2,4-triazol-3-ylsulfanyl)ethyl]pyrrolo[3,4-c]carbazole-1,3(2H,6H)-dione,
9-hydroxy-6-(2-hydroxyethyl)-4-phenylpyrrolo[3,4-c]carbazole-1,3(2H,6H)-dione,
6-(3-bromopropyl)-4-(2,6-dichlorophenyl)-9-hydroxypyrrolo[3,4-c]carbazole-1,3(2H,6H)-dione,
4-(2-chlorophenyl)-9-hydroxy-6-(3-methoxypropyl)pyrrolo[3,4-c]carbazole-1,3(2H,6H)-dione,
4-(2-chlorophenyl)-9-hydroxy-6-(2-hydroxypropyl)pyrrolo[3,4-c]carbazole-1,3(2H,6H)-dione,
4-(2-chlorophenyl)-9-hydroxy-6-[(2S)-3-hydroxy-2-methylpropyl]pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(1H-imidazol-5-yl)ethyl]propanamide,
9-hydroxy-6-(3-hydroxypropyl)-4-(2-methoxyphenyl)pyrrolo[3,4-c]carbazole-1,3(2H,6H)-dione,
methyl 3-(4-(2-chlorophenyl)-9-hydroxy-1,3-dioxo-2,3-dihydropyrrolo[3,4-c]carbazol-6(1H)-yl)propanoate,
3-(4-(2-chlorophenyl)-9-hydroxy-1,3-dioxo-2,3-dihydropyrrolo[3,4-c]carbazol-6(1H)-yl)-N-[2-(4-morpholinyl)ethyl]propanamide,
4-(4-(2-chlorophenyl)-9-hydroxy-1,3-dioxo-2,3-dihydropyrrolo[3,4-c]carbazol-6(1H)-yl]butanenitrile,
4-(2-chloro-6-methoxyphenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-6-(3,4-dihydroxybutyl)-9-hydroxypyrrolo[3,4-c]carbazole-1,3(2H,6H)-dione,
3-(4-(2-chloro-6-methoxyphenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-9-hydroxy-6-[(2R)-3-hydroxy-2-methylpropyl]pyrrolo[3,4-c]carbazole-1,3(2H,6H)-dione,
2-(4-(2-chlorophenyl)-9-hydroxy-1,3-dioxo-2,3-dihydropyrrolo[3,4-c]carbazol-6(1H)-yl)ethylmethanesulfonate,
4-(2-chloro-6-methoxyphenyl)-9-hydroxy-6-(3-hydroxypropyl)pyrrolo[3,4-c]carbazole-1,3(2H,6H)-dione,
9-hydroxy-6-(2-hydroxyethyl)-4-(2-methoxyphenyl)pyrrolo[3,4-c]carbazole-1,3(2H,6H)-dione,
4-(2-chlorophenyl)-6-(2-hydroxyethyl)-9-hydroxypyrrolo[3,4-c]carbazole-1,3(2H,6H)-dione,
4-(2-chlorophenyl)-9-hydroxy-6-[3-(methylsulfanyl)propyl]pyrrolo[3,4-c]carbazole-1,3(2H,6H)-dione,
4-(2-chlorophenyl)-6-ethyl-9-hydroxypyrrolo[3,4-c]carbazole-1,3(2H,6H)-dione,
4-(2-chlorophenyl)-9-hydroxy-6-isopropylpyrrolo[3,4-c]carbazole-1,3(2H,6H)-dione,
4-(2-chlorophenyl)-9-hydroxy-6-[3-(1H-imidazol-1-yl)propyl]pyrrolo[3,4-c]carbazole-1,3(2H,6H)-dione,
4-(2-chloro-6-methoxyphenyl)-9-hydroxy-6-[3-(4-morpholinyl)propyl]pyrrolo[3,4-c]carbazole-1,3(2H,6H)-dione,
6-(2-chloroethyl)-4-(2-chlorophenyl)-9-hydroxypyrrolo[3,4-c]carbazole-1,3(2H,6H)-dione,
6-(3-bromopropyl)-4-(2-chloro-6-methoxyphenyl)-9-hydroxypyrrolo[3,4-c]carbazole-1,3(2H,6H)-dione,
4-(2-chlorophenyl)-9-hydroxy-6-[2-hydroxy-3-(methylamino)propyl]pyrrolo[3,4-c]carbazole-1,3(2H,6H)-dione,
4-(2-chlorophenyl)-9-hydroxy-6-methylpyrrolo[3,4-c]carbazole-1,3(2H,6H)-dione,
4-(2-chlorophenyl)-9-hydroxy-6-[2-hydroxy-3-(4-morpholinyl)propyl]pyrrolo[3,4-c]carbazole-1,3(2H,6H)-dione, and
4-(2,6-dichlorophenyl)-9-hydroxy-6-[3-(1H-imidazol-1-yl)propyl]pyrrolo[3,4-c]carbazole-1,3(2H,6H)-dione
described in the specification of JP 2006-504632 A.

Examples of the Chk1 inhibitor include a kinase (e.g., Chk1) inhibitor UCN-01, a Chk1 inhibitor SCH900776, GDC-0425, XL844, CEP-3891, CHIR-124, CHIR-600, PF-00394691, PF-00477736, N-aryl-N'-pyrazinylurea, Go6976, SB-218078, ICP-1, PD-0166285, CBP-501, staurosporine, isogranulatimide, debromohymenialdisine (DBH), scytonemin, pyrimidine, pyrrolopyrimidine, pyrazolopyrimidine, furanopyrimidine, pyrazoloquinoline, imidazopyrazine, pyrimidinylindazolylamine, 2-ureidothiophene, 3-ureidothiophene, triazolone, diarylurea, benzimidazole quinolone, dibenzodiazepinone, indolinone, aminopyrazole, indenopyrazole, and diazepinoindolone.

Examples of the Hsp90 inhibitor include geldanamycin, tanespimycin (17-AAG), 17-aminodemethoxygeldanamycin (IPI-493), 17-dimethylaminoethylamino-17-demethoxygeldanamycin (17-DMAG), XL888, SNX-2112, SNX-5422, SNX-7081, ganetespib (STA-9090), AT13387, AUY922, Debio0932, BIIB028, BIIBO21, MPC-3100, MPC-0767, retaspimycin (IPI-504), PU3, PU24FCI, PU-H58, PU-H71, DS-2248, KW-2478, CCT018159, CCT0129397, BJ-B11, elesclomol (STA-4783), G3130, gedunin, herbimycin, radester, KNK437, HSP990, and NVP-BEP800.

Examples of the Myt1 inhibitor include:
2-(4-fluorophenylamino)-4-(4-pyridyl)thiazole,
2-(4-fluorophenylamino)-4-(4-fluorophenyl)thiazole,
3-(3,4-dichlorophenyl)-5-[4-[2-[(2-pyridyl)amino]thiazolyl]]-isoxazole, and
3-(3,4-dichlorophenyl)-5-[4-[2-(3-pyridyl)amino]thiazolyl]-isoxazole,
which are compounds described in JP 2002-531500 A;
1,4-bis(2-phenylamino-4-thiazolyl)benzene,
1,4-bis(2-phenylamino-4-thiazolyl)benzene dihydrobromide,
1-[2-phenyl-4-(5-bromo)thiazolyl]-4-[2-phenyl-4-thiazolyl]benzene,
1-[2-phenyl-4-(5-bromo)thiazolyl]-4-[2-phenyl-4-thiazolyl]benzene dihydrobromide,
1,4-bis(2-phenyl)-(4-(5-bromo)thiazolylbenzene,
1,4-bis(2-phenyl)-(4-(5-bromo)thiazolylbenzene dihydrobromide,
1,4-bis(2-(3-pyridylamino)-4-thiazolyl)benzene,
1,4-bis(2-(3-pyridylamino)-4-thiazolyl)benzene bistrifluoroacetate,
1-[(2-(3-pyridylamino)-4-(5-bromo)thiazolyl)]-4-[2-(3-pyridylamino)-4-thiazolyl]benzene,
1-[(2-(3-pyridylamino)-4-(5-bromo)thiazolyl)]-4-[2-(3-pyridylamino)-4-thiazolyl]benzene bistrifluoroacetate,
1,3-bis(2-(3-pyridylamino)-4-thiazolyl)benzene,
1,3-bis(2-(3-pyridylamino)-4-thiazolyl)benzene dihydrobromide,
1,4-bis(2-(2-pyridylamino)-4-thiazolyl)benzene,
1,4-bis(2-(2-pyridylamino)-4-thiazolyl)benzene dihydrobromide,
1,3-bis(2-(2-pyridylamino)-4-thiazolyl)benzene,
1,3-bis(2-(2-pyridylamino)-4-thiazolyl)benzene dihydrobromide,
4,4'-di(2,2-phenylaminothiazolyl),
4,4'-di(2,2-phenylaminothiazolyl) dihydrobromide, 4,4'-di(2-(2-methoxypyrid-5-ylamino)thiazolyl),
4,4'-di(2-(2-methoxypyrid-5-ylamino)thiazolyl) bistrifluoroacetate,
4,4'-di(2-(2-pyridyl)aminothiazolyl), and
4,4'-di(2-(2-pyridyl)aminothiazolyl) bistrifluoroacetate,
which are compounds described in JP 2002-531503 A;
bis[2-(4-phenyl-5-methyl)thiazolyl]amine,
bis[2-(4-phenyl-5-methyl)thiazolyl]amine hydrobromide,
bis[2-(4-(2-pyridyl)thiazolyl]amine,
bis[2-(4-(2-pyridyl)thiazolyl]amine dihydrobromide,
bis[2-[4-(3-pyridyl)thiazolyl]amine,
bis[2-[4-(3-pyridyl)thiazolyl]amine bistrifluoroacetate,
N,N-bis(5(3,4-dichlorophenyl)-2-thiazolyl)amine,
N,N-bis(5(3,4-dichlorophenyl)-2-thiazolyl)amine dihydrobromide,
1,3-bis[4-(3-pyridyl)-2-thiazolylamino]benzene, and
1,3-bis[4-(3-pyridyl)-2-thiazolylamino]benzene dihydrobromide,
which are compounds described in JP 2002-531504 A; and dasatinib.

The compound (I) according to the present invention or the pharmaceutically acceptable salt thereof can be used as a pharmaceutical drug, particularly, an antitumor agent, in the form of a conventional pharmaceutical preparation for oral administration or parenteral administration such as instillation.

The preparation for oral administration includes: solid preparations such as tablets, granules, powders, and capsules; and liquid preparations such as syrups. These preparations can be prepared by conventional methods. The solid preparations can be prepared by using conventional pharmaceutical carriers such as lactose, starch (e.g., corn starch), crystalline cellulose (e.g., microcrystalline cellulose), hydroxypropylcellulose, calcium carboxymethylcellulose, talc, and magnesium stearate. The capsules can be prepared by the encapsulation of the granules or the powders thus prepared. The syrups can be prepared by the dissolution or suspension of the compound (I) according to the present invention or the pharmaceutically acceptable salt thereof in an aqueous solution containing sucrose, carboxymethylcellulose, or the like.

The preparation for parenteral administration includes injections for instillation. The injection preparations can also be prepared by a conventional method and can be appropriately incorporated into a tonicity agent (e.g., mannitol, sodium chloride, glucose, sorbitol, glycerol, xylitol, fructose, maltose, and mannose), a stabilizer (e.g., sodium sulfide and albumin), and an antiseptic (e.g., benzyl alcohol and methyl p-hydroxybenzoate).

The compound (I) according to the present invention or the pharmaceutically acceptable salt thereof is pharmaceutically effective and is particularly effective for the treatment of tumor. Examples of the tumor include: solid tumors such as breast cancer, colon cancer, and lung cancer; and blood cancers such as leukemia, lymphoma, and myeloma.

The compound (I) according to the present invention or the pharmaceutically acceptable salt thereof is effective for suppressing a wide range of cancer types.

The dose of the compound (I) according to the present invention or the pharmaceutically acceptable salt thereof can vary according to the severity of a disease, the age and body weight of a patient, a dosage form, etc. The daily dose in an adult is usually in the range of 1 mg to 1,000 mg, which can be administered in one portion or in two or three divided potions through an oral route or a parenteral route.

The ratio between the Cdc7 inhibitor and the M-phase promoter in the pharmaceutical composition of the present invention is 1:300 to 10:1, preferably 1:100 to 3:1, more preferably 1:30 to 1.2:1.

EXAMPLES

Interaction Between Cdc7 Inhibitor and M-phase Promoter (Wee1 Inhibitor)

In order to examine the synergistic effect of a Cdc7 inhibitor and an M-phase promoter, a Wee1 inhibitor MK-1775 was coadministered with the Cdc7 inhibitor (compound I-D or compound I-E).

The present inventor had previously demonstrated that the cytotoxicity of a particular Cdc7 inhibitor to Colo205 is decreased by its coadministration with paclitaxel, and confirmed that a compound, such as paclitaxel, which inhibits the G2/M-phase, cannot be used in a favorable concomitant drug with a particular Cdc7 inhibitor. Accordingly, the influence of the Wee1 inhibitor MK-1775 and the Cdc7 inhibitor in combination on the viability of Colo205 was studied.

Cultured Cells

COLO205 (RCB2127, RIKEN BRC) was cultured in a 10-cm dish using an RPMI-1640 medium (Sigma-Aldrich Corp., R8758) supplemented with 10% FCS (Equitech-Bio, Inc.) and 5% penicillin-streptomycin (GIBCO/Thermo Fisher Scientific, Inc., 15140). The medium was removed from the cells in a well grown state (70 to 90% confluent), and the cells were dissociated from the dish by treatment with 2 mL of trypsin (TrypL Express, manufactured by GIBCO/Thermo Fisher Scientific, Inc.) and recovered into the same medium as above.

Panc-1 (ATCC, CRL-1469) was cultured in a 10-cm dish using a D-MEM medium (Sigma-Aldrich Corp., D5796) supplemented with 10% FCS (Equitech-Bio, Inc.) and 5% penicillin-streptomycin (GIBCO/Thermo Fisher Scientific, Inc., 15140). The medium was removed from the cells in a well grown state (70 to 90% confluent), and the cells were dissociated from the dish by treatment with 2 mL of trypsin (TrypL Express, manufactured by GIBCO/Thermo Fisher Scientific, Inc.) and recovered into the same medium as above.

NHDF cells (Cryo NHDF-NeoCC-2509, manufactured by Sanko Junyaku Co., Ltd.) were cultured in a 10-cm dish using a medium (Brett Kit FGM2, CLCC-3132). The medium was removed from the NHDF cells in a well grown state (70 to 90% confluent), and the cells were washed with 5 mL of HEPES-buffered saline in a subculture reagent set (CLCC-5034, manufactured by Sanko Junyaku Co., Ltd.).

After removal of the HEPES-buffered saline, the whole dish was covered with 3 mL of a trypsin/EDTA solution included in the set. The cells were dissociated from the dish by giving a small impact on the side of the dish with taps of a hand. Then, 3 mL of a trypsin-neutralizing solution included in the set was added to the cells, which were then recovered.

Addition of Compounds to Cultured Cells

The recovered cells of each line were seeded at $2.5 \times 10^5$ cells/ml/well to a 6-well plate (BD Falcon, catalog No. 353046). The cells were cultured overnight in a 5% $CO_2$ incubator. On the next day, 500 µl of a medium supplemented with 1.5 µl of a stock solution having a 1000-fold concentration of each compound to be added was added to each well, and the cells were further cultured for 48 to 72 hours under conditions involving a final concentration of 1 µM.

Study on Influence on Cell Cycle

After the reaction of the cells with the compound for 48 to 72 hours, the cells were dissociated from the well by treatment with trypsin (TrypL Express, manufactured by GIBCO/Thermo Fisher Scientific, Inc.) and washed with DPBS. Then, 1 ml of cold ethanol was added thereto, and the cells were stored at −30° C. until staining. The cells were washed with DPBS once before staining and left standing with a propidium iodide (PI) solution at room temperature for 30 minutes or longer in the dark. The cells stained with PI were studied for the cell cycle and the rate of cell death indicated by SubG1 using FACS.

First, the concentration of MK-1775 was examined for the upregulation of phosphorylated histone H3. Subsequently, the Cdc7 inhibitor and MK-1775 were added within the concentration range that would promote the M-phase to the cultures of the colon cancer cells Colo205 cells.

Evaluation of Synergistic Effect of Drugs Used in Combination Using BLISS Score

The BLISS scoring is a criterion often used in the evaluation of the synergistic effect of drugs used in combination (Borisy et al., Proc. Natl. Acad. Sci. USA. 100 (13): 7977-7982 (2003); and Buck et al., Mol. Cancer. Ther. 5 (11) (2006)). This BLISS scoring was used to analyze the effect of the Cdc7 inhibitor and the Wee1 inhibitor used in combination on the inhibition of cancer cell growth.

Example 1

Interaction Between Compound (I-D) or Compound (I-E) as Cdc7 Inhibitor and Wee1 Inhibitor as M-phase Promoter in Combination Specifically, 0.1 µM of compound (I-D) was coadministered with DMSO (control) or 0.25 µM, 0.5 µM, and 0.75 µM each of the Wee1 inhibitor MK-1775 to Colo205 cells, and the number of cells that died was examined. Also, 0.1 µM of compound (I-E) was coadministered with DMSO (control) or each concentration of MK-1775 to the cells, and the number of cells that died was examined. The results are shown in FIG. 1.

The cell death induced by compound (I-D) or compound (I-E) was found to be synergistically increased by the coadministration with the Wee1 inhibitor.

MK-1775 in the concentration range of 0.1 to 1 µM efficiency increased the proportion of cells in the M-phase. Actually, synergistic increase was observed in the ratio of the killed cells to the cells treated with MK-1775 and compound (I-D) or compound (I-E) in combination.

Example 2

Cancer Cell Selectivity of Interaction Between Compound (I-D) or Compound (I-E) and MK-1775 (Wee1 Inhibitor)

In order to examine whether the synergistic effect of compound (I-D) or compound (I-E) and MK-1775 (Wee1 inhibitor) would be observed in normal cells, normal human skin fibroblast (NHDF) cells were treated with the combination drug and examined.

The NHDF cells were treated with compound (I-D) or compound (I-E) and varying concentrations of MK-1775 in combination.

Specifically, 0.1 µM of compound (I-D) was coadministered with DMSO (control) or 0.25 µM, 0.5 µM, and 0.75 µM each of MK-1775 to NHDF cells, and the number of cells that died was examined. Also, 0.1 µM of compound (I-E) was coadministered with DMSO (control) or each concentration of MK-1775 to the cells, and the number of cells that died was examined. The results are shown in FIG. 2.

The examination of compound (I-D) or compound (I-E) at a concentration of 0.1 µM showed no increase in cytotoxicity to the NHDF cells as normal cells even supplemented with the Wee1 inhibitor MK-1775, demonstrating that the effect brought about by the combination of compound (I-D) or compound (I-E) and MK-1775 is selective for cancer cells.

Example 3

Interaction Between Compound (I-D) or Compound (I-E) and MK-1775 in Panc-1 Cells (Pancreatic Cancer Cell Line)

Specifically, 0.1 µM of compound (I-D) was coadministered with DMSO (control) or 0.5 µM and 0.75 µM each of MK-1775 to pancreatic cancer cell line Panc-1 cells, and the number of cells that died was examined. Also, 0.1 µM of compound (I-E) was coadministered with DMSO (control) or each concentration of MK-1775 to the cells, and the number of cells that died was examined. The results are shown in FIG. 3. The cell death of the Panc-1 cells (pancreatic cancer cell line) induced by compound (I-D) or compound (I-E) was also found to be synergistically increased by the coadministration with the Wee1 inhibitor.

Example 4

Variation in Effect Depending on Composition of Compound (I-D) or Compound (I-E) and MK-1775 in Combination Drug While the composition (ratio by µM) of compound (I-E) and MK-1775 in the combination drug was changed within the range of 1:100 to 3:1, such as 0.01:1.0, 0.03:0.1, and 0.3:0.1, compound (I-E) and MK-1775 were coadministered to Colo205 cells, and the number of cells that died was examined. The results are shown in FIG. 4. In the range of compound (I-E):MK-1775=1:100 to 3:1, the cell death induced by compound (I-E) was found to be sufficiently synergistically increased by the coadministration with the Wee1 inhibitor.

Example 5

Interaction Between Compound (I-A) and MK-1775 in Combination

A Cdc7 inhibitor was coadministered with MK-1775 to Colo205 cells, and the number of cells that died was examined, in the same way as in Example 1 except that compound (I-A) was used as the Cdc7 inhibitor. The results are shown in FIG. 5. Even when compound (I-A) was used as a different Cdc7 inhibitor, the induced cell death was found to be synergistically increased by the coadministration with the Wee1 inhibitor MK-1775.

Example 6

Interaction Between Compound (I-B) and MK-1775 in Combination

A Cdc7 inhibitor was coadministered with MK-1775 to Colo205 cells, and the number of cells that died was examined, in the same way as in Example 1 except that compound (I-B) was used as the Cdc7 inhibitor, and the concentration of compound (I-B) was set to 0.3 µM. The results are shown in FIG. 6. Even when compound (I-B) was used as a different Cdc7 inhibitor, the induced cell death was found to be synergistically increased by the coadministration with the Wee1 inhibitor MK-1775.

Example 7

Interaction Between Compound (I-C) and MK-1775 in Combination

A Cdc7 inhibitor was coadministered with MK-1775 to Colo205 cells, and the number of cells that died was examined, in the same way as in Example 1 except that compound (I-C) was used as the Cdc7 inhibitor, and the concentration of compound (I-C) was set to 0.1 μM or 0.3 μM. The results are shown in FIG. 7. Even when compound (I-C) was used, the induced cell death was found to be synergistically increased by the coadministration with the Wee1 inhibitor MK-1775.

Example 8

Interaction Between Compound (I-F) or Compound (I-G) and MK-1775 in Combination

A Cdc7 inhibitor was coadministered with MK-1775 to Colo205 cells, and the number of cells that died was examined, in the same way as in Example 1 except that: compound (I-F) or compound (I-G) was used as the Cdc7 inhibitor; the concentration thereof was set to 0.1 μM or 0.3 μM; and the concentration of MK-1775 was set to 0.5 μM. The results are shown in FIG. 8. Even when compound (I-F) or compound (I-G) was used, the induced cell death was found to be synergistically increased by the coadministration with the Wee1 inhibitor MK-1775. In this context, the compound (I-G) is compound F26 described in the specifications of JP 2009-531373 A and International Publication No. WO 2007/110344, and the compound (I-F) is a Cdc7/Cdk9 inhibitor of Merck KGaA (catalog No.: 217707-5MGCN), as mentioned above.

Example 9

Interaction Between Compound (I-D) or Compound (I-E) and Different M-phase Promoter in Combination A Cdc7 inhibitor and an M-phase promoter were coadministered in combination to Colo205 cells, and the number of cells that died was examined, in the same way as in Example 1 except that: compound (I-D) or compound (I-E) was used as the Cdc7 inhibitor; the concentration thereof was set to 0.3 μM or 0.1 μM; a Chk1 inhibitor SCH900776 was used instead of the Wee1 inhibitor MK-1775 as the M-phase promoter; and the concentration thereof was set to 3.3 μM. The results are shown in FIG. 9. Even when SCH900776 (SCH) was used as a different M-phase promoter, the induced cell death was found to be synergistically increased by the coadministration with compound (I-D) or compound (I-E).

Example 10

Interaction Between Compound (I-D) or Compound (I-E) and Different M-phase Promoter in Combination A Cdc7 inhibitor and an M-phase promoter were coadministered in combination to Colo205 cells, and the number of cells that died was examined, in the same way as in Example 1 except that: compound (I-D) or compound (I-E) was used as the Cdc7 inhibitor; the concentration thereof was set to 0.1 μM, 0.03 μM, or 0.3 μM; a Chk1 inhibitor UCN-01 was used instead of the Wee1 inhibitor MK-1775 as the M-phase promoter; and the concentration thereof was set to 333 nM. The results are shown in FIG. 10. Even when UCN-01 was used as a different M-phase promoter, the induced cell death was found to be synergistically increased by the coadministration with compound (I-D) or compound (I-E).

Example 11

Interaction Between Compound (I-D) or Compound (I-E) and Different M-phase Promoter in Combination A Cdc7 inhibitor and an M-phase promoter were coadministered in combination to Colo205 cells, and the number of cells that died was examined, in the same way as in Example 1 except that: compound (I-D) or compound (I-E) was used as the Cdc7 inhibitor; the concentration thereof was set to 0.1 μM, 0.03 μM, or 0.3 μM; an Hsp90 inhibitor geldanamycin was used instead of the Wee1 inhibitor MK-1775 as the M-phase promoter; and the concentration thereof was set to 10 nM or 33 nM. The results are shown in FIG. 11. Even when geldanamycin was used as a different M-phase promoter, the induced cell death was found to be synergistically increased by the coadministration with compound (I-D) or compound (I-E).

Example 12

Evaluation of Interaction Between Compound (I-D) or Compound (I-E) and Wee1 Inhibitor as M-phase Promoter in Combination Using BLISS Score The BLISS scoring was used to analyze the effect of the Cdc7 inhibitor and the Wee1 inhibitor (MK-1775) used in combination on the inhibition of cancer cell growth.
(Culture of Cells Used)
Human mammary gland cancer MDA-MB-231 cells (ATCC No. HTB-26) were cultured in a T75 flask using a Leibovitz's L-15 medium (Life Technologies Corp., #11415-064) supplemented with 10% fetal bovine serum (FBS) (Equitech-Bio, Inc.) and 5% penicillin-streptomycin (Nacalai Tesque, Inc.) (hereinafter, referred to as a growth medium) in a 37° C. incubator (without $CO_2$).
(Inoculation of Cell Suspension to Plate)
The MDA-MB-231 cells were resuspended at a cell density of $0.035 \times 10^6$ cells/mL in a fresh growth medium. Then, the cell suspension was added at 100 μL/well to a 96-well cell culture plate (Falcon, #353075) and cultured overnight in a 37° C. incubator (3,500 cells per well). Approximately 24 hours after the inoculation, the medium was removed, and 80 μL of a fresh growth medium was added to each well.
(Addition of Compound to be Tested)
A 10 mM DMSO stock solution of a first test compound Cdc7 inhibitor (compound (I-D) or compound (I-E) was diluted into 10 concentrations (10 mM, 5 mM, 2.5 mM, 1.25 mM, 0.625 mM, 0.313 mM, 0.156 mM, 0.0781 mM, 0.0391 mM, and 0.0195 mM) with DMSO. Each solution was further diluted 100-fold with a growth medium and added at 10 μL/well to the plate (1000-fold dilution; final administration concentration range: 19.5 to 10000 nM). A 10 mM DMSO stock solution of a second test compound Wee1 inhibitor (MK-1775) was diluted into 8 concentrations (1 mM, 0.5 mM, 0.25 mM, 0.125 mM, 0.0625 mM, 0.0313 mM, 0.0156 mM, and 0.00781 mM) with DMSO. Each solution was further diluted 100-fold with a growth medium and added at 10 μL/well to the plate (1000-fold dilution; final administration concentration range: 7.81 to 1000 nM). Also, DMSO was diluted 100-fold with a growth medium and added at 20 μL/well to the plate (control wells).

(Measurement of Cell Growth Inhibitory Effect)

After the addition of the compounds, the cells were incubated for 72 hours. Then, Mildform® 10N (Wako Pure Chemical Industries, Ltd., #133-10311) was added at 100 μL/well and incubated at room temperature for 45 minutes to fix the cells. Each well was washed with 100 μL of phosphate-buffered saline (PBS) three times. Hoechst 33342 (Life Technologies Corp., #H3570) diluted into 2 μM with PBS was added at 100 μL/well and incubated at room temperature for 30 minutes to stain the nuclei. Each well was washed with 100 μL of PBS three times. Then, the number of nuclei (the number of cells) was measured using a cell image analyzer (ArrayScan VTI HCS Reader, Thermo Fischer Scientific, Inc.) (Ex/Em=350/461 nm).

(Calculation of Cell Growth Inhibitory Effect)

After 72 hours, the average number from the control wells was used as the number of untreated control cells ($G_{unt72}$), and the average number from the compound-treated wells was used as the number of compound-treated cells ($G_{72}$). Wells in which the medium was merely replaced 24 hours after the cell inoculation were counted as an initial value and used as the initial number of cells ($G_0$).

The rate of cell growth in each well was calculated according to the following expression:

Rate of cell growth $G=((G_{72}-G_0)/(G_{unt72}-G_0))$

The percent rate of inhibition of cell growth in each well was calculated according to the following expression, and the results are shown in FIGS. 12 and 13:

Rate of inhibition of cell growth $GI$ (%)=100×(1−$G$)

(Evaluation Based on BLISS Score)

Assuming that the first test compound and the second test compound each acted as a single agent (i.e., the rate of cell growth when the concentration of either of the compounds was 0), the theoretical BLISS independence ($BLISS_{in}$) of each well can be calculated according to the following expression:

$BLISS_{in}=G$(First test compound)×$G$(Second test compound)

The BLISS score of each well can be determined from the difference between the theoretical value $BLISS_{in}$ and the actually measured value of the rate of cell growth. If the BLISS score is a positive number, the synergistic effect appears to be present.

BLISS score=100×($BLISS_{in}$−$G$)

The results of this test are shown in FIGS. 14 and 15.

These results indicate that the combined use of the Cdc7 inhibitor compound (I-D) or compound (I-E) and the Wee1 inhibitor (MK-1775) synergistically inhibits the growth of cancer cells.

INDUSTRIAL APPLICABILITY

The present invention provides an anticancer composition of a Cdc7 inhibitor and an M-phase promoter that brings about cell death more efficiently with higher selectivity and specificity for a wide range of cancer cells, as compared with use of the Cdc7 inhibitor or the M-phase promoter alone.

The invention claimed is:

1. A pharmaceutical composition comprising a Cdc7 inhibitor and an M-phase promoter, wherein the Cdc7 inhibitor is a furanone derivative represented by the following formula (I):

[Chemical Formula 1]

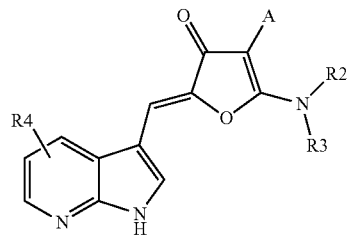

(I)

wherein A represents —COOR1;

R1 represents a hydrogen atom or an optionally substituted hydrocarbon group selected from a linear or branched alkyl group having 1 to 6 carbon atoms, a linear or branched alkenyl group having 1 to 6 carbon atoms, an alkynyl group having 2 to 6 carbon atoms, a cycloalkyl group having 3 to 8 carbon atoms, a cycloalkenyl group having 3 to 8 carbon atoms, an aralkyl group whose aryl moiety is aryl having 6 to 14 carbon atoms and whose alkylene moiety is a group in which one hydrogen atom has been removed from the alkyl group;

one of R2 and R3 represents a hydrogen atom, or an optionally substituted hydrocarbon group selected from a linear or branched alkyl group having 1 to 6 carbon atoms, a linear or branched alkenyl group having 1 to 6 carbon atoms, an alkynyl group having 2 to 6 carbon atoms, a cycloalkyl group having 3 to 8 carbon atoms, a cycloalkenyl group having 3 to 8 carbon atoms, and an aralkyl group whose aryl moiety is aryl having 6 to 14 carbon atoms and whose alkylene moiety is a group in which one hydrogen atom has been removed from the alkyl group; and the other represents a phenyl group optionally having a substituent, a heterocyclic ring optionally having a substituent, or a heterocyclic fused ring optionally having a substituent; and R4 represents a hydrogen atom or a halogen atom;

wherein the optional substituent(s) on the hydrocarbon group, heterocycle, phenyl or heterocyclic fused ring is one or more groups selected from halogen, substituted or unsubstituted alkyl, substituted or unsubstituted alkoxy, substituted or unsubstituted amino, nitro, cyano, hydroxy, substituted or unsubstituted alkylamino, carbamoyl, carboxy, formyl, acetyl and benzoyl;

or a pharmaceutically acceptable salt thereof; and wherein the M phase promoter is selected from a Wee1 inhibitor, a Chk1 inhibitor, an Hsp90 inhibitor and an Myt1 inhibitor.

2. The pharmaceutical composition according to claim 1 wherein the furanone derivative has the structure of the following:

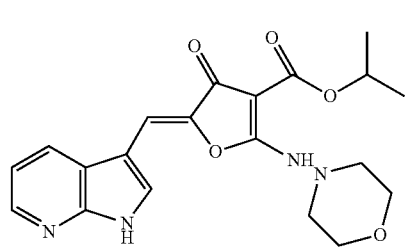

(I-A)

-continued

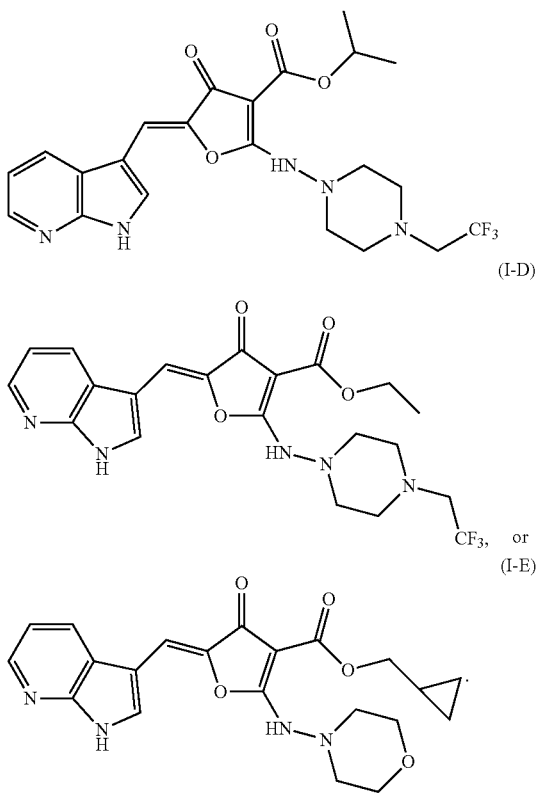

3. The pharmaceutical composition according to claim 1, wherein the M-phase promoter is a Wee1 inhibitor.

4. The pharmaceutical composition according to claim 3, wherein the Wee1 inhibitor is

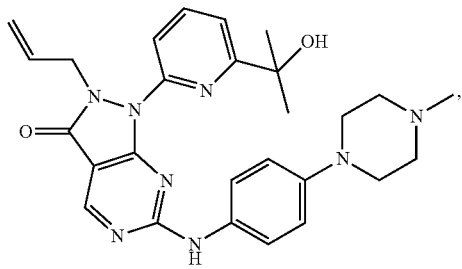 [SMILES: C=CCn1c(=O)c2cnc(Nc3ccc(N4CCN(C)CC4)cc3)nc2n1-c1cccc(C(C)(C)O)n1]

miR-424, miR-381,
6-butyl-4-(2-chlorophenyl)-9-hydroxypyrrolo[3,4-c]carbazole-1,3-(2H,6H)-dione,
9-methoxy-4-(2-methoxy-5-nitrophenyl)-4,5,6,10c-tetrahydropyrrolo[3,4-c]carbazole-1,3(2H,3aH)-dione,
N-[3-(4-(2-chlorophenyl)-9-hydroxy-1,3-dioxo-2,3-dihydropyrrolo[3,4-c]carbazol-6(1H)-yl)propanoyl]benzenesulfonamide,
4-(2,6-dichlorophenyl)-9-hydroxy-6-(3-hydroxypropyl)pyrrolo[3,4-c]carbazole-1,3(2H,6H)-dione,
4-(2,6-dichlorophenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-(1H)-yl)-N-(1H-tetrazol-5-yl)propanamide,
4-(2-chlorophenyl)-9-hydroxy-6-[2-(1H-1,2,4-triazol-5-ylsulfinyl)ethyl]pyrrolo[3,4-c]carbazole-1,3(2H,6H)-dione,
6-(3-bromopropyl)-4-(2-chlorophenyl)-9-hydroxypyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)propanoic acid,
N-[3-(4-(2-chlorophenyl)-9-hydroxy-1,3-dioxo-2,3-dihydropyrrolo[3,4-c]carbazol-6(1H)-yl)propanoyl]-2-(dimethylamino)ethanesulfonamide,
4-(2-chlorophenyl)-9-hydroxypyrrolo[3,4-c]carbazole-1,3(2H,6H)-dione,
N-[3-(4-(2-chlorophenyl)-9-hydroxy-1,3-dioxo-2,3-dihydropyrrolo[3,4-c]carbazol-6(1H)-yl)propanoyl]methanesulfonamide,
4'-(4-(2-chlorophenyl)-9-hydroxy-1,3-dioxo-2,3-dihydropyrrolo[3,4-c]carbazol-6(1H)-yl)butanoic acid,
N-[4-(4-(2-chlorophenyl)-9-hydroxy-1,3-dioxo-2,3-dihydropyrrolo[3,4-c]carbazol-6(1H)-yl)butanoyl]methanesulfonamide,
6-acetyl-4-(2-chlorophenyl)-9-hydroxypyrrolo[3,4-c]carbazole-1,3(2H,6H)-dione,
3-(4-(2,6-dichlorophenyl)-9-hydroxy-1,3-dioxo-2,3-dihydropyrrolo[3,4-c]carbazol-6(1H)-yl)-N-[2-(dimethylamino)ethyl]propanamide,
3-(4-(2-chlorophenyl)-9-hydroxy-1,3-dioxo-2,3-dihydropyrrolo[3,4-c]carbazol-6(1H)-yl)propanenitrile,
4-(2-chlorophenyl)-9-hydroxy-6-[3-(1H-tetrazol-5-yl)propyl]pyrrolo[3,4-c]carbazole-1,3(2H,6H)-dione,
4-(2-chlorophenyl))-9-hydroxy-6-[2-(1H-imidazol-2-ylsulfanyl)ethyl]pyrrolo[3,4-c]carbazole-1,3(2H,6H)-dione,
N-[4-(4-(2-chlorophenyl)-9-hydroxy-1,3-dioxo-2,3-dihydropyrrolo[3,4-c]carbazol-6(1H)-yl)butanoyl]benzenesulfonamide,
4-(2-chlorophenyl)-9-hydroxy-6-[2-(1H-1,2,4-triazol-5-ylsulfonyl)ethyl]pyrrolo[3,4-c]carbazole-1,3(2H,6H)-dione,
4-(2-chlorophenyl)-9-hydroxy-6-[2-(1H-imidazol-2-ylsulfinyl)ethyl]pyrrolo[3,4-c]carbazole-1,3(2H,6H)-dione,
4-(2-chlorophenyl)-9-hydroxy-6-[2-(1H-tetrazol-5-yl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanamide,
4-(2-chlorophenyl)-9-hydroxy-6-[2-(1H-imidazol-2-ylsulfonyl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanoic acid,
4-(2-chlorophenyl)-6-(2,3-dihydroxypropyl)-9-hydroxypyrrolo[3,4-c]carbazole-1,3(2H, 6H)-dione,
2-(4-(2,6-dichlorophenyl)-9-hydroxy-1,3-dioxo-2,3-dihydropyrrolo[3,4-c]carbazol-6(1H)-yl)ethylmethanesulfonate,
4-(2-chlorophenyl)-9-hydroxy-6-[2-(4H-1,2,4-triazol-3-ylsulfanyl)ethyl]pyrrolo[3,4-c]carbazole-1,3(2H,6H)-dione,
9-hydroxy-6-(2-hydroxyethyl)-4-phenylpyrrolo[3,4-c]carbazole-1,3(2H,6H)-dione,
6-(3-bromopropyl)-4-(2,6-dichlorophenyl)-9-hydroxypyrrolo[3,4-c]carbazole-1,3(2H,6H)-dione,
4-(2-chlorophenyl)-9-hydroxy-6-(3-methoxypropyl)pyrrolo[3,4-c]carbazole-1,3(2H,6H)-dione,
4-(2-chlorophenyl)-9-hydroxy-6-(2-hydroxypropyl)pyrrolo[3,4-c]carbazole-1,3(2H,6H)-dione, 4-(2-chlorophenyl)-9-hydroxy-6-[(2S)-3-hydroxy-2-methylpropyl]pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(1H-imidazol-5-yl)ethyl]propanamide,
9-hydroxy-6-(3-hydroxypropyl)-4-(2-methoxyphenyl)pyrrolo[3,4-c]carbazole-1,3(2H,6H)-dione,
methyl 3-(4-(2-chlorophenyl)-9-hydroxy-1,3-dioxo-2,3-dihydropyrrolo[3,4-c]carbazol-6(1H)-yl)propanoate,
3-(4-(2-chlorophenyl)-9-hydroxy-1,3-dioxo-2,3-dihydropyrrolo[3,4-c]carbazol-6(1H)-yl)-N-[2-(4-morpholinyl)ethyl]propanamide,
4-(4-(2-chlorophenyl)-9-hydroxy-1,3-dioxo-2,3-dihydropyrrolo[3,4-c]carbazol-6(1H)-yl]butanenitrile,
4-(2-chloro-6-methoxyphenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-6-(3,4-dihydroxybutyl)-9-hydroxypyrrolo[3,4-c]carbazole-1,3(2H,6H)-dione,
3-(4-(2-chloro-6-methoxyphenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-9-hydroxy-6-[(2R)-3-hydroxy-2-methylpropyl]pyrrolo[3,4-c]carbazole-1,3(2H,6H)-dione,
2-(4-(2-chlorophenyl)-9-hydroxy-1,3-dioxo-2,3-dihydropyrrolo[3,4-c]carbazol-6(1H)-yl)ethylmethanesulfonate,
4-(2-chloro-6-methoxyphenyl)-9-hydroxy-6-(3-hydroxypropyl)pyrrolo[3,4-c]carbazole-1,3(2H,6H)-dione,
9-hydroxy-6-(2-hydroxyethyl)-4-(2-methoxyphenyl)pyrrolo[3,4-c]carbazole-1,3(2H,6H)-dione,
4-(2-chlorophenyl)-6-(2-hydroxyethyl)-9-hydroxypyrrolo[3,4-c]carbazole-1,3(2H,6H)-dione,
4-(2-chlorophenyl)-9-hydroxy-6-[3-(methylsulfanyl)propyl]pyrrolo[3,4-c]carbazole-1,3(2H,6H)-dione,
4-(2-chlorophenyl)-6-ethyl-9-hydroxypyrrolo[3,4-c]carbazole-1,3(2H,6H)-dione,
4-(2-chlorophenyl)-9-hydroxy-6-isopropylpyrrolo[3,4-c]carbazole-1,3(2H,6H)-dione,
4-(2-chlorophenyl)-9-hydroxy-6-[3-(1H-imidazol-1-yl)propyl]pyrrolo[3,4-c]carbazole-1,3(2H,6H)-dione,
4-(2-chloro-6-methoxyphenyl)-9-hydroxy-6-[3-(4-morpholinyl)propyl]pyrrolo[3,4-c]carbazole-1,3(2H,6H)-dione,
6-(2-chloroethyl)-4-(2-chlorophenyl)-9-hydroxypyrrolo[3,4-c]carbazole-1,3(2H,6H)-dione,
6-(3-bromopropyl)-4-(2-chloro-6-methoxyphenyl)-9-hydroxypyrrolo[3,4-c]carbazole-1,3(2H,6H)-dione,
4-(2-chlorophenyl)-9-hydroxy-6-[2-hydroxy-3-(methylamino)propyl]pyrrolo[3,4-c]carbazole-1,3(2H,6H)-dione,
4-(2-chlorophenyl)-9-hydroxy-6-methylpyrrolo[3,4-c]carbazole-1,3(2H,6H)-dione,
4-(2-chlorophenyl)-9-hydroxy-6-[2-hydroxy-3-(4-morpholinyl)propyl]pyrrolo[3,4-c]carbazole-1,3(2H,6H)-dione, or
4-(2,6-dichlorophenyl)-9-hydroxy-6-[3-(1H-imidazol-1-yl)propyl]pyrrolo[3,4-c]carbazole-1,3(2H,6H)-dione.

5. The pharmaceutical composition according to claim 1, wherein the M-phase promoter is a Chk1 inhibitor, an Hsp90 inhibitor, or a Myt1 inhibitor.

6. The pharmaceutical composition according to claim 5, wherein the Chk1 inhibitor is SCH900776, UCN-01, GDC-0425, XL844, CEP-3891, CHIR-124, CHIR-600, PF-00394691, PF-00477736, N-aryl-N'-pyrazinylurea, Go6976, SB-218078, ICP-1, PD-0166285, CBP-501, staurosporine, isogranulatimide, debromohymenialdisine (DBH), scytonemin, pyrimidine, pyrrolopyrimidine, pyrazolopyrimidine, furanopyrimidine, pyrazoloquinoline, imidazopyrazine, pyrimidinylindazolylamine, 2-ureidothiophene, 3-ureidothiophene, triazolone, diarylurea, benzimidazole quinolone, dibenzodiazepinone, indolinone, aminopyrazole, indenopyrazole, or diazepinoindolone.

7. The pharmaceutical composition according to claim 5, wherein the Hsp90 inhibitor is geldanamycin, tanespimycin (17-AAG), 17-aminodemethoxygeldanamycin (IPI-493), 17-dimethylaminoethylamino-17-demethoxygeldanamycin (17-DMAG), XL888, SNX-2112, SNX-5422, SNX-7081, ganetespib (STA-9090), AT13387, AUY922, Debio0932, BIIB028, BIIB021, MPC-3100, MPC-0767, retaspimycin (IPI-504), PU3, PU24FCI, PU-H58, PU-H71, DS-2248, KW-2478, CCT018159, CCT0129397, BJ-B11, elesclomol (STA-4783), G3130, gedunin, herbimycin, radester, KNK437, HSP990, or NVP-BEP800.

8. The pharmaceutical composition according to claim 5, wherein the Myt1 inhibitor is
2-(4-fluorophenylamino)-4-(4-pyridyl)thiazole,
2-(4-fluorophenylamino)-4-(4-fluorophenyl)thiazole,
3-(3,4-dichlorophenyl)-5-[4-[2-[(2-pyridyl)amino]thiazolyl]]-isoxazole,
3-(3,4-dichlorophenyl)-5-[4-[2-(3-pyridyl)amino]thiazolyl]-isoxazole,
1,4-bis(2-phenylamino-4-thiazolyl)benzene,
1,4-bis(2-phenylamino-4-thiazolyl)benzene dihydrobromide,
1-[2-phenyl-4-(5-bromo)thiazolyl]-4-[2-phenyl-4-thiazolyl]benzene,
1-[2-phenyl-4-(5-bromo)thiazolyl]-4-[2-phenyl-4-thiazolyl]benzene dihydrobromide,
1,4-bis(2-phenyl)-(4-(5-bromo)thiazolylbenzene,
1,4-bis(2-phenyl)-(4-(5-bromo)thiazolylbenzene dihydrobromide,
1,4-bis(2-(3-pyridylamino)-4-thiazolyl)benzene,
1,4-bis(2-(3-pyridylamino)-4-thiazolyl)benzene bistrifluoroacetate,
1-[(2-(3-pyridylamino)-4-(5-bromo)thiazolyl)]-4-[2-(3-pyridylamino)-4-thiazolyl]benzene,
1-[(2-(3-pyridylamino)-4-(5-bromo)thiazolyl)]-4-[2-(3-pyridylamino)-4-thiazolyl]benzene bistrifluoroacetate,
1,3-bis(2-(3-pyridylamino)-4-thiazolyl)benzene,
1,3-bis(2-(3-pyridylamino)-4-thiazolyl)benzene dihydrobromide,
1,4-bis(2-(2-pyridylamino)-4-thiazolyl)benzene,
1,4-bis(2-(2-pyridylamino)-4-thiazolyl)benzene dihydrobromide,
1,3-bis(2-(2-pyridylamino)-4-thiazolyl)benzene,
1,3-bis(2-(2-pyridylamino)-4-thiazolyl)benzene dihydrobromide,
4,4'-di(2,2-phenylaminothiazolyl),
4,4'-di(2,2-phenylaminothiazolyl) dihydrobromide,
4,4'-di(2-(2-methoxypyrid-5-ylamino)thiazolyl),
4,4'-di(2-(2-methoxypyrid-5-ylamino)thiazolyl) bistrifluoroacetate,
4,4'-di(2-(2-pyridyl)aminothiazolyl),
4,4'-di(2-(2-pyridyl)aminothiazolyl) bistrifluoroacetate,
bis[2-(4-phenyl-5-methyl)thiazolyl]amine,
bis[2-(4-phenyl-5-methyl)thiazolyl]amine hydrobromide,
bis[2-(4-(2-pyridyl)thiazolyl]amine,
bis[2-(4-(2-pyridyl)thiazolyl]amine dihydrobromide,
bis[2-[4-(3-pyridyl)thiazolyl]amine, bis[2-[4-(3-pyridyl)thiazolyl)amine bistrifluoroacetate,
N,N-bis(5(3,4-dichlorophenyl)-2-thiazolyl)amine,
N,N-bis(5(3,4-dichlorophenyl)-2-thiazolyl)amine dihydrobromide,
1,3-bis[4-(3-pyridyl)-2-thiazolylamino]benzene,
1,3-bis[4-(3-pyridyl)-2-thiazolylamino]benzene dihydrobromide, or dasatinib.

9. A method of treating cancer in a subject, comprising administering an effective amount of a Cdc7 inhibitor and an M-phase promoter to the subject, wherein the Cdc7 inhibitor is a furanone derivative represented by the following formula (I):

[Chemical Formula 1]

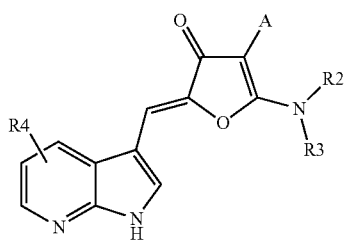

(I)

wherein A represents —COOR1;
R1 represents a hydrogen atom or an optionally substituted hydrocarbon group selected from a linear or branched alkyl group having 1 to 6 carbon atoms, a linear or branched alkenyl group having 1 to 6 carbon atoms, an alkynyl group having 2 to 6 carbon atoms, a cycloalkyl group having 3 to 8 carbon atoms, a cycloalkenyl group having 3 to 8 carbon atoms, an aralkyl group whose aryl moiety is aryl having 6 to 14 carbon atoms and whose alkylene moiety is a group in which one hydrogen atom has been removed from the alkyl group;
one of R2 and R3 represents a hydrogen atom, or an optionally substituted hydrocarbon group selected from a linear or branched alkyl group having 1 to 6 carbon atoms, a linear or branched alkenyl group having 1 to 6 carbon atoms, an alkynyl group having 2 to 6 carbon atoms, a cycloalkyl group having 3 to 8 carbon atoms, a cycloalkenyl group having 3 to 8 carbon atoms, and an aralkyl group whose aryl moiety is aryl having 6 to 14 carbon atoms and whose alkylene moiety is a group in which one hydrogen atom has been removed from the alkyl group; and the other represents a phenyl group optionally having a substituent, a heterocyclic ring optionally having a substituent, or a heterocyclic fused ring optionally having a substituent; and
R4 represents a hydrogen atom or a halogen atom;
wherein the optional substituent(s) on the hydrocarbon group, heterocycle, phenyl or heterocyclic fused ring is one or more groups selected from halogen, substituted or unsubstituted alkyl, substituted or unsubstituted alkoxy, substituted or unsubstituted amino, nitro, cyano, hydroxy, substituted or unsubstituted alkylamino, carbamoyl, carboxy, formyl, acetyl and benzoyl;
or a pharmaceutically acceptable salt thereof; and
wherein the M phase promoter is selected from a Wee1 inhibitor, a Chk1 inhibitor, an Hsp90 inhibitor and an Myt1 inhibitor, and
the cancer is selected from the group consisting of lung, leukemia, lymphoma, myeloma, ovarian, colon, pancreatic, and breast cancer.

10. The method of claim 9, wherein the cancer is lung cancer.

11. The method of claim 9, wherein the administration is oral and/or intravenous.

12. The method of claim 9, wherein the furanone derivative has the structure of the following:

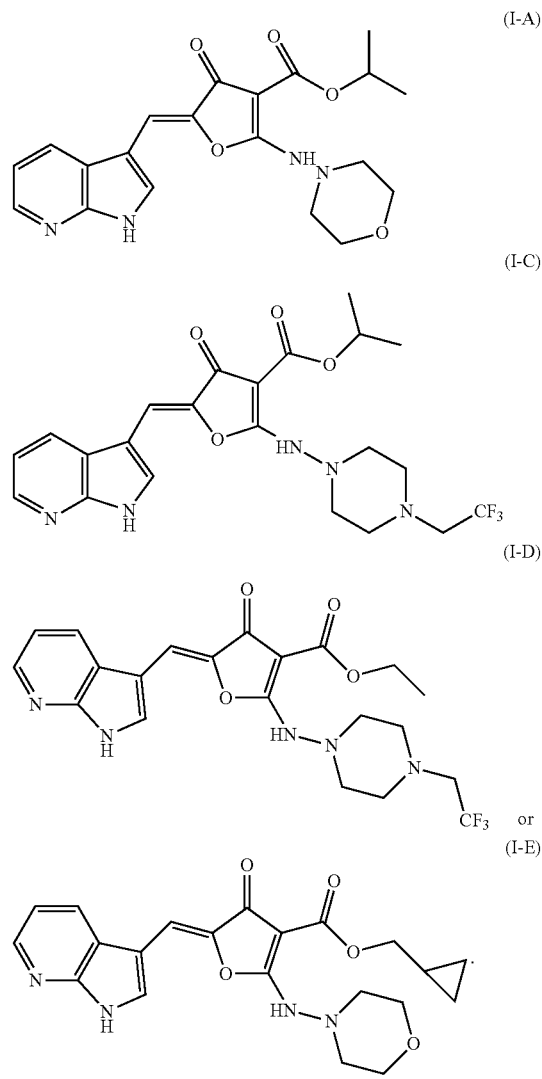

13. The method of claim 9, wherein the M-phase promoter is a Wee1 inhibitor selected from

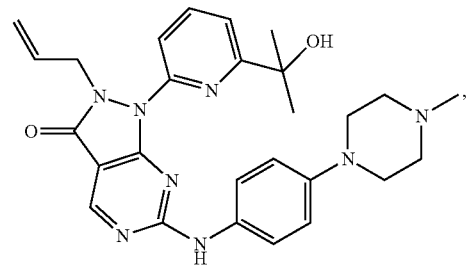 [SMILES: C=CCn1c(=O)c2cnc(Nc3ccc(N4CCN(C)CC4)cc3)nc2n1-c1cccc(C(C)(C)O)n1]

miR-424, miR-381,
6-butyl-4-(2-chlorophenyl)-9-hydroxypyrrolo[3,4-c]carbazole-1,3-(2H,6H)-dione,
9-methoxy-4-(2-methoxy-5-nitrophenyl)-4,5,6,10c-tetrahydropyrrolo[3,4-c]carbazol-1,3(2H,3aH)-dione, N-[3-(4-(2-chlorophenyl)-9-hydroxy-1,3-dioxo-2,3-dihydropyrrolo[3,4-c]carbazol-6(1H)-yl)propanoyl]benzenesulfonamide,
4-(2,6-dichlorophenyl)-9-hydroxy-6-(3-hydroxypropyl)pyrrolo[3,4-c]carbazole-1,3(2H,6H)-dione,
4-(2,6-dichlorophenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-(1H)-yl)-N-(1H-tetrazol-5-yl)propanamide,
4-(2-chlorophenyl)-9-hydroxy-6-[2-(1H-1,2,4-triazol-5-ylsulfinyl)ethyl]pyrrolo[3,4-c]carbazole-1,3(2H,6H)-dione,
6-(3-bromopropyl)-4-(2-chlorophenyl)-9-hydroxypyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)propanoic acid,
N-[3-(4-(2-chlorophenyl)-9-hydroxy-1,3-dioxo-2,3-dihydropyrrolo[3,4-c]carbazol-6(1H)-yl)propanoyl]-2-(dimethylamino)ethanesulfonamide,
4-(2-chlorophenyl)-9-hydroxypyrrolo[3,4-c]carbazole-1,3(2H,6H)-dione,
N-[3-(4-(2-chlorophenyl)-9-hydroxy-1,3-dioxo-2,3-dihydropyrrolo[3,4-c]carbazol-6(1H)-yl)propanoyl]methanesulfonamide,
4'-(4-(2-chlorophenyl)-9-hydroxy-1,3-dioxo-2,3-dihydropyrrolo[3,4-c]carbazol-6(1H)-yl)butanoic acid,
N-[4-(4-(2-chlorophenyl)-9-hydroxy-1,3-dioxo-2,3-dihydropyrrolo[3,4-c]carbazol-6(1H)-yl)butanoyl]methanesulfonamide,
6-acetyl-4-(2-chlorophenyl)-9-hydroxypyrrolo[3,4-c]carbazole-1,3(2H,6H)-dione,
3-(4-(2,6-dichlorophenyl)-9-hydroxy-1,3-dioxo-2,3-dihydropyrrolo[3,4-c]carbazol-6(1H)-yl)-N-[2-(dimethylamino)ethyl]propanamide,
3-(4-(2-chlorophenyl)-9-hydroxy-1,3-dioxo-2,3-dihydropyrrolo[3,4-c]carbazol-6(1H)-yl)propanenitrile,
4-(2-chlorophenyl)-9-hydroxy-6-[3-(1H-tetrazol-5-yl)propyl]pyrrolo[3,4-c]carbazole-1,3(2H,6H)-dione,
4-(2-chlorophenyl))-9-hydroxy-6-[2-(1H-imidazol-2-ylsulfanyl)ethyl]pyrrolo[3,4-c]carbazole-1,3(2H,6H)-dione,
N-[4-(4-(2-chlorophenyl)-9-hydroxy-1,3-dioxo-2,3-dihydropyrrolo[3,4-c]carbazol-6(1H)-yl)butanoyl]benzenesulfonamide,
4-(2-chlorophenyl)-9-hydroxy-6-[2-(1H-1,2,4-triazol-5-ylsulfonyl)ethyl]pyrrolo[3,4-c]carbazole-1,3(2H,6H)-dione,
4-(2-chlorophenyl)-9-hydroxy-6-[2-(1H-imidazol-2-ylsulfinyl)ethyl]pyrrolo[3,4-c]carbazole-1,3(2H,6H)-dione,
4-(2-chlorophenyl)-9-hydroxy-6-[2-(1H-tetrazol-5-yl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanamide,
4-(2-chlorophenyl)-9-hydroxy-6-[2-(1H-imidazol-2-ylsulfonyl)ethyl]pyrrolo[3,4-c]carbazole-1,3(2H,6H)-dione,
3-(9-hydroxy-1,3-dioxo-4-phenyl-2,3-dihydropyrrolo[3,4-c]carbazol-6(1H)-yl)propanoic acid,
4-(2-chlorophenyl)-6-(2,3-dihydroxypropyl)-9-hydroxypyrrolo[3,4-c]carbazole-1,3(2H,6H)-dione,
2-(4-(2,6-dichlorophenyl)-9-hydroxy-1,3-dioxo-2,3-dihydropyrrolo[3,4-c]carbazol-6(1H)-yl)ethanemethanesulfonate,
4-(2-chlorophenyl)-9-hydroxy-6-[2-(4H-1,2,4-triazol-3-ylsulfanyl)ethyl]pyrrolo[3,4-c]carbazole-1,3(2H,6H)-dione,
9-hydroxy-6-(2-hydroxyethyl)-4-phenylpyrrolo[3,4-c]carbazole-1,3(2H,6H)-dione,
6-(3-bromopropyl)-4-(2,6-dichlorophenyl)-9-hydroxypyrrolo[3,4-c]carbazole-1,3(2H, 6H)-dione,
4-(2-chlorophenyl)-9-hydroxy-6-(3-methoxypropyl)pyrrolo[3,4-c]carbazole-1,3(2H, 6H)-dione,
4-(2-chlorophenyl)-9-hydroxy-6-(2-hydroxypropyl)pyrrolo[3,4-c]carbazole-1,3(2H, 6H)-dione,
4-(2-chlorophenyl)-9-hydroxy-6-[(2S)-3-hydroxy-2-methylpropyl]pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(1H-imidazol-5-yl)ethyl]propanamide,
9-hydroxy-6-(3-hydroxypropyl)-4-(2-methoxyphenyl)pyrrolo [3,4-c]carbazole-1,3(2H, 6H)-dione,
methyl 3-(4-(2-chlorophenyl)-9-hydroxy-1,3-dioxo-2,3-dihydropyrrolo[3,4-c]carbazol-6(1H)-yl)propanoate,
3-(4-(2-chlorophenyl)-9-hydroxy-1,3-dioxo-2,3-dihydropyrrolo[3,4-c]carbazol-6(1H)-yl)-N-[2-(4-morpholinyl)ethyl]propanamide,
4-(2-chlorophenyl)-9-hydroxy-1,3-dioxo-2,3-dihydropyrrolo[3,4-c]carbazol-6(1H)-yl]butanenitrile,
4-(2-chloro-6-methoxyphenyl)-9-hydroxy-6-(2-hydroxyethyl)pyrrolo[3,4-c]carbazole-1,3(2H,6H)-dione,
3-(4-(2-chlorophenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-6-(3,4-dihydroxybutyl)-9-hydroxypyrrolo[3,4-c]carbazole-1,3(2H, 6H)-dione,
3-(4-(2-chloro-6-methoxyphenyl)-9-hydroxy-1,3-dioxo-2,3-dihydropyrrolo[3,4-c]carbazol-6(1H)-yl)-N-[2-(dimethylamino)ethyl]propanamide,
4-(2-chlorophenyl)-9-hydroxy-6-[(2R)-3-hydroxy-2-methylpropyl]pyrrolo[3,4-c]carbazole-1,3(2H,6H)-dione,
2-(4-(2-chlorophenyl)-9-hydroxy-1,3-dioxo-2,3-dihydropyrrolo[3,4-c]carbazol-6(1H)-yl)ethylmethanesulfonate,
4-(2-chloro-6-methoxyphenyl)-9-hydroxy-6-(3-hydroxypropyl)pyrrolo[3,4-c]carbazole-1,3(2H,6H)-dione,
9-hydroxy-6-(2-hydroxyethyl)-4-(2-methoxyphenyl)pyrrolo[3,4-c]carbazole-1,3(2H,6H)-dione,
4-(2-chlorophenyl)-6-(2-hydroxyethyl)-9-hydroxypyrrolo[3,4-c]carbazole-1,3(2H,6H)-dione,
4-(2-chlorophenyl)-9-hydroxy-6-[3-(methylsulfanyl)propyl]pyrrolo[3,4-c]carbazole-1,3(2H,6H)-dione,
4-(2-chlorophenyl)-6-ethyl-9-hydroxypyrrolo[3,4-c]carbazole-1,3(2H,6H)-dione,
4-(2-chlorophenyl)-9-hydroxy-6-isopropylpyrrolo[3,4-c]carbazole-1,3(2H,6H)-dione,
4-(2-chlorophenyl)-9-hydroxy-6[3-(1H-imidazol-1-yl)propyl]pyrrolo[3,4-c]carbazole-1,3(2H,6H)-dione,
4-(2-chloro-6-methoxyphenyl)-9-hydroxy-6-[3-(4-morpholinyl)propyl]pyrrolo[3,4-c]carbazole-1,3(2H,6H)-dione,
6-(2-chloroethyl)-4-(2-chlorophenyl)-9-hydroxypyrrolo[3,4-c]carbazole-1,3(2H,6H)-dione,
6-(3-bromopropyl)-4-(2-chloro-6-methoxyphenyl)-9-hydroxypyrrolo[3,4-c]carbazole-1,3(2H,6H)-dione,
4-(2-chlorophenyl)-9-hydroxy-6-[2-hydroxy-3-(methylamino)propyl]pyrrolo[3,4-c]carbazole-1,3(2H,6H)-dione, 4-(2-chlorophenyl)-9-hydroxy-6-methylpyrrolo[3,4-c]
carbazole-1,3(2H,6H)-dione,
4-(2-chlorophenyl)-9-hydroxy-6-[2-hydroxy-3-(4-morpholinyl)propyl]pyrrolo[3,4-c]carbazole-1,3(2H,6H)-dione, and
4-(2,6-dichlorophenyl)-9-hydroxy-6-[3-(1H-imidazol-1-yl)propyl]pyrrolo[3,4-c]carbazole-1,3(2H,6H)-dione.

14. The method of claim 9, wherein the M-phase promoter is the Chk1 inhibitor selected from SCH900776, UCN-01, GDC-0425, XL844, CEP-3891, CHIR-124, CHIR-600, PF-00394691, PF-00477736, N-aryl-N'-pyrazinylurea, Go6976, SB-218078, ICP-1, PD-0166285, CBP-501, staurosporine, isogranulatimide, debromohymenialdisine (DBH), scytonemin, pyrimidine, pyrrolopyrimidine, pyrazolopyrimidine, furanopyrimidine, pyrazoloquinoline, imidazopyrazine, pyrimidinylindazolylamine, 2-ureidothiophene, 3-ureidothiophene, triazolone, diarylurea, benzimidazole quinolone, dibenzodiazepinone, indolinone, aminopyrazole, indenopyrazole, and diazepinoindolone.

15. The method of claim 9, wherein the M-phase inhibitor is an Hsp90 inhibitor selected from geldanamycin, tanespimycin (17-AAG), 17-aminodemethoxygeldanamycin (IPI-493), 17-dimethylaminoethylamino-17-demethoxygeldanamycin (17-DMAG), XL888, SNX-2112, SNX-5422, SNX-7081, ganetespib (STA-9090), AT13387, AUY922, Debio0932, BIIB028, BIIB021, MPC-3100, MPC-0767, retaspimycin (IPI-504), PU3, PU24FCI, PU-H58, PU-H71, DS-2248, KW-2478, CCT018159, CCT0129397, BJ-B11, elesclomol (STA-4783), G3130, gedunin, herbimycin, radester, KNK437, HSP990, and NVP-BEP800.

16. The method of claim 9, wherein the M-phase inhibitor is an Myt1 inhibitor selected from:
2-(4-fluorophenylamino)-4-(4-pyridyl)thiazole,
2-(4-fluorophenylamino)-4-(4-fluorophenyl)thiazole,
3-(3,4-dichlorophenyl)-5-[4-2-[(2-pyridyl)amino]thiazolyl]]-isoxazole,
3-(3,4-dichlorophenyl)-5-[4-[2-(3-pyridyl)amino]thiazolyl]-isoxazole,
1,4-bis(2-phenylamino-4-thiazolyl)benzene,
1,4-bis(2-phenylamino-4-thiazolyl)benzene dihydrobromide,
1-[2-phenyl-4-(5-bromo)thiazolyl]-4-[2-phenyl-4-thiazolyl]benzene,
1-[2-phenyl-4-(5-bromo)thiazolyl]-4[2-phenyl-4-thiazolyl]benzene dihydrobromide,
1,4-bis(2-phenyl)-(4-(5-bromo)thiazolylbenzene,
1,4-bis(2-phenyl)-(4-(5-bromo)thiazolylbenzene dihydrobromide,
1,4-bis(2-(3-pyridylamino)-4-thiazolyl)benzene,
1,4-bis(2-(3-pyridylamino)-4-thiazolyl)benzene bistrifluoroacetate,
1-[(2-(3-pyridylamino)-4-(5-bromo)thiazolyl)]-4-[2-(3-pyridylamino)-4-thiazolyl]benzene,
1-[(2-(3-pyridylamino)-4-(5-bromo)thiazolyl)]-4-[2-(3-pyridylamino)-4-thiazolyl]benzene bistrifluoroacetate,
1,3-bis(2-(3-pyridylamino)-4-thiazolyl)benzene,
1,3-bis(2-(3-pyridylamino)-4-thiazolyl)benzene dihydrobromide,
1,4-bis(2-(2-pyridylamino)-4-thiazolyl)benzene,
1,4-bis(2-(2-pyridylamino)-4-thiazolyl)benzene dihydrobromide,
1,3-bis(2-(2-pyridylamino)-4-thiazolyl)benzene,
1,3-bis(2-(2-pyridylamino)-4-thiazolyl)benzene dihydrobromide,
4,4'-di(2,2-phenylaminothiazolyl),
4,4'-di(2,2-phenylaminothiazolyl) dihydrobromide,
4,4'-di(2-(2-methoxypyrid-5-ylamino)thiazolyl),
4,4'-di(2-(2-methoxypyrid-5-ylamino)thiazolyl) bistrifluoroacetate,
4,4'-di(2-(2-pyridyl)aminothiazolyl),
4,4'-di(2-(2-pyridyl)aminothiazolyl) bistrifluoroacetate,
bis[2-(4-phenyl-5-methyl)thiazolyl]amine,
bis[2-(4-phenyl-5-methyl)thiazolyl]amine hydrobromide,
bis[2-(4-(2-pyridyl)thiazolyl]amine,
bis[2-(4-(2-pyridyl)thiazolyl]amine dihydrobromide,
bis[2-[4-(3-pyridyl)thiazolyl]amine,
bis[2-[4-(3-pyridyl)thiazolyl]amine bistrifluoroacetate,
N,N-bis(5(3,4-dichlorophenyl)-2-thiazolyl)amine,
N,N-bis(5(3,4-dichlorophenyl)-2-thiazolyl)amine dihydrobromide,
1,3-bis[4-(3-pyridyl)-2-thiazolylamino]benzene,
1,3-bis[4-(3-pyridyl)-2-thiazolylamino]benzene dihydrobromide, and dasatinib.

* * * * *